(12) United States Patent
Vetter et al.

(10) Patent No.: US 10,702,191 B2
(45) Date of Patent: Jul. 7, 2020

(54) DETERMINATION OF A CURRENTLY TREATED BODY PORTION OF A USER

(71) Applicant: Braun GmbH, Kronberg (DE)

(72) Inventors: Ingo Vetter, Egelsbach (DE); Carl Stückrath, Friedberg (DE); Hansjorg Reick, Bad Soden (DE); Jens-Uwe Garbas, Erlangen (DE); Jochen Seitz, Erlangen (DE); Andreas Ernst, Erlangen (DE); Marcus Bocksch, Erlangen (DE)

(73) Assignee: BRAUN GMBH, Kronberg (DE)

( * ) Notice: Subject to any disclaimer, the term of this patent is extended or adjusted under 35 U.S.C. 154(b) by 207 days.

(21) Appl. No.: 15/246,465

(22) Filed: Aug. 24, 2016

(65) Prior Publication Data

US 2017/0069083 A1  Mar. 9, 2017

(30) Foreign Application Priority Data

Sep. 8, 2015 (EP) .................................... 15184240

(51) Int. Cl.
*A61B 5/11* (2006.01)
*A46B 15/00* (2006.01)
*G06K 9/62* (2006.01)

(52) U.S. Cl.
CPC ........ *A61B 5/1128* (2013.01); *A46B 15/0006* (2013.01); *G06K 9/6293* (2013.01); *A46B 2200/102* (2013.01); *A46B 2200/1066* (2013.01); *G06K 2209/055* (2013.01)

(58) Field of Classification Search
None
See application file for complete search history.

(56) References Cited

U.S. PATENT DOCUMENTS

| | | |
|---|---|---|
| 942,708 A | 12/1909 | Blot |
| 3,783,364 A | 1/1974 | Gallanis et al. |
| 4,716,614 A | 1/1988 | Jones |
| 5,561,881 A | 10/1996 | Klinger et al. |
| 5,701,629 A | 12/1997 | O'Brien |
| 5,796,325 A | 8/1998 | Lundell et al. |

(Continued)

FOREIGN PATENT DOCUMENTS

| | | |
|---|---|---|
| DE | 19506129 A1 | 8/1996 |
| DE | 102008027317 A1 | 12/2009 |

(Continued)

OTHER PUBLICATIONS

International Search Report and Written Opinion for PCT/IB2016/053892 dated Sep. 2, 2016.

(Continued)

*Primary Examiner* — Chikaodili E Anyikire
(74) *Attorney, Agent, or Firm* — Vladimir Vitenberg

(57) ABSTRACT

An apparatus for determining a body portion of a user treated by the user using a personal hygienic device. The apparatus includes a camera configured to capture the user to obtain a pictorial representation of the user while treating the body portion using the personal hygienic device; an interface configured to receive sensor data from at least one inertial sensor residing in the personal hygienic device; and an analyzer configured to analyze the pictorial representation and the sensor data to determine the body portion.

15 Claims, 12 Drawing Sheets

(56) References Cited

U.S. PATENT DOCUMENTS

| | | | |
|---|---|---|---|
| 5,864,288 A | 1/1999 | Hogan | |
| 5,930,858 A | 8/1999 | Jung | |
| 5,944,531 A | 8/1999 | Foley | |
| 6,102,284 A | 8/2000 | Myers et al. | |
| 6,519,579 B1 | 2/2003 | Plankensteiner et al. | |
| 6,536,068 B1* | 3/2003 | Yang | A46B 15/0002 15/105 |
| 6,611,780 B2 | 8/2003 | Lundell et al. | |
| 6,752,627 B2 | 6/2004 | Lin | |
| 6,754,928 B1 | 6/2004 | Rosen | |
| 6,808,298 B2 | 10/2004 | Christensen | |
| 6,902,397 B2 | 6/2005 | Farrell et al. | |
| 7,024,717 B2 | 4/2006 | Hilscher et al. | |
| 7,411,511 B2 | 8/2008 | Kennish et al. | |
| 7,748,069 B2 | 7/2010 | Dawley | |
| 7,890,193 B2 | 2/2011 | Tingey | |
| 7,976,388 B2 | 7/2011 | Park et al. | |
| 8,175,840 B2 | 5/2012 | Hwang | |
| 8,176,591 B2 | 5/2012 | Iwahori et al. | |
| 8,201,295 B2 | 6/2012 | Gatzemeyer et al. | |
| 8,320,682 B2 | 11/2012 | Froeba et al. | |
| 8,341,791 B2 | 1/2013 | Iwahori | |
| 8,393,037 B2 | 3/2013 | Iwahori et al. | |
| 8,479,341 B2 | 7/2013 | Iwahori | |
| 8,544,131 B2 | 10/2013 | Braun et al. | |
| 8,743,051 B1 | 6/2014 | Moy et al. | |
| 8,744,192 B2 | 6/2014 | Ortins et al. | |
| 9,174,351 B2 | 11/2015 | Binder | |
| 9,848,174 B2 | 12/2017 | Binder | |
| 9,950,434 B2 | 4/2018 | Binder | |
| 9,950,435 B2 | 4/2018 | Binder | |
| 10,064,711 B1 | 9/2018 | Richter | |
| 10,220,529 B2 | 3/2019 | Binder | |
| 10,449,681 B2 | 10/2019 | Binder | |
| 2002/0133308 A1 | 9/2002 | Lundell | |
| 2003/0115694 A1 | 6/2003 | Pace | |
| 2004/0019990 A1 | 2/2004 | Farrell | |
| 2004/0053190 A1 | 3/2004 | Lin | |
| 2005/0000044 A1 | 1/2005 | Hilscher et al. | |
| 2006/0040246 A1 | 2/2006 | Ding | |
| 2006/0096046 A1 | 5/2006 | Hilscher | |
| 2007/0136964 A1 | 6/2007 | Dawley | |
| 2007/0182571 A1 | 8/2007 | Kennish | |
| 2007/0234493 A1 | 10/2007 | Hilscher et al. | |
| 2007/0270221 A1 | 11/2007 | Park | |
| 2008/0010771 A1 | 1/2008 | Hilscher et al. | |
| 2008/0022469 A1 | 1/2008 | Hilscher | |
| 2008/0022470 A1 | 1/2008 | Hilscher | |
| 2008/0022471 A1 | 1/2008 | Hilscher | |
| 2008/0022501 A1 | 1/2008 | Hilscher | |
| 2008/0022503 A1 | 1/2008 | Hilscher | |
| 2008/0028549 A1 | 2/2008 | Hilscher | |
| 2008/0032265 A1 | 2/2008 | Hilscher | |
| 2008/0109973 A1 | 5/2008 | Farrell et al. | |
| 2008/0196185 A1 | 8/2008 | Gatzemeyer | |
| 2008/0313829 A1 | 12/2008 | Dabrowski | |
| 2009/0092955 A1 | 4/2009 | Hwang | |
| 2009/0130636 A1 | 5/2009 | Hwang | |
| 2009/0143914 A1 | 6/2009 | Cook et al. | |
| 2009/0291422 A1 | 11/2009 | Puurunen | |
| 2009/0317770 A1 | 12/2009 | Gatzemeyer | |
| 2010/0281636 A1* | 11/2010 | Ortins | A46B 9/04 15/4 |
| 2011/0010875 A1 | 1/2011 | Iwahori et al. | |
| 2011/0010876 A1* | 1/2011 | Iwahori | A46B 15/0002 15/22.1 |
| 2011/0041269 A1* | 2/2011 | Iwahori | A46B 15/0006 15/22.1 |
| 2011/0146016 A1* | 6/2011 | Gatzemeyer | A46B 13/023 15/167.1 |
| 2012/0151697 A1 | 6/2012 | Farrell et al. | |
| 2012/0266397 A1 | 10/2012 | Iwahori et al. | |
| 2012/0310593 A1 | 12/2012 | Bates | |
| 2014/0065588 A1* | 3/2014 | Jacobson | G09B 23/283 434/263 |
| 2014/0246049 A1 | 9/2014 | Ikkink et al. | |
| 2015/0044629 A1 | 2/2015 | Wang | |
| 2016/0235357 A1 | 8/2016 | Ohmer | |
| 2016/0374609 A1 | 12/2016 | Vetter et al. | |
| 2017/0065386 A1 | 3/2017 | Farrell et al. | |
| 2017/0069083 A1 | 3/2017 | Vetter et al. | |
| 2017/0236298 A1 | 8/2017 | Vetter | |
| 2017/0238692 A1 | 8/2017 | Sarubbo | |
| 2018/0192765 A1 | 7/2018 | Jeanne | |

FOREIGN PATENT DOCUMENTS

| | | |
|---|---|---|
| DE | 102009048117 A1 | 4/2011 |
| DE | 102009048118 A1 | 4/2011 |
| EP | 1593001 B1 | 6/2012 |
| EP | 2833325 A1 | 2/2015 |
| EP | 2406697 B1 | 4/2016 |
| EP | 3141151 A1 | 3/2017 |
| EP | 3238565 | 11/2017 |
| FR | 2832298 A1 | 5/2003 |
| JP | 09168428 | 6/1997 |
| JP | 11346833 A | 12/1999 |
| JP | 2003534095 A | 11/2003 |
| JP | 2011146049 | 7/2011 |
| WO | WO2006137648 A1 | 12/2006 |
| WO | WO2007032015 A2 | 3/2007 |
| WO | WO2007112112 A1 | 10/2007 |
| WO | WO2011073010 A1 | 6/2011 |
| WO | WO2014103412 A1 | 7/2014 |
| WO | WO2014202438 A1 | 12/2014 |
| WO | WO2016020803 A1 | 2/2016 |

OTHER PUBLICATIONS

Bocksch, M. et al. Pedestrian Activity Classification to Improve Human Tracking and Localization. In: Proceedings of the 4th International Conference on Indoor Positioning and Indoor Navigation (IPIN), 2013, S. 667-671.

International Search Report and Written Opinion for PCT/IB2016/055244 dated Sep. 1, 2016.

European Search Report for 16155933.1-1901 dated Jul. 20, 2016.

DeMenthon, D.F. et al. "Model-Based Object Pose in 25 Lines of Code", Computer Vision Laboratory, ECCV 1992, pp. 335-343.

Ernst, A. et al. "Fast face detection and species classification of African great apes", AVSS 2011, IEEE 8th International Conference on Advanced Video and Signal-based Surveillance.

Kueblbeck, C. et al. "Face detection and tracking in video sequences using the modified census transformation", Journal on Image and Visiong Computing, vol. 24, issue 6, pp. 564-572, 2006.

Saragih, J et al. "Deformable Model Fitting by Regularized Landmark Mean'Shifts", International Journal of Computer Vision, 2011 91: 200-215.

Search Report for PCT/US2007/023677 dated Aug. 27, 2008.

\* cited by examiner

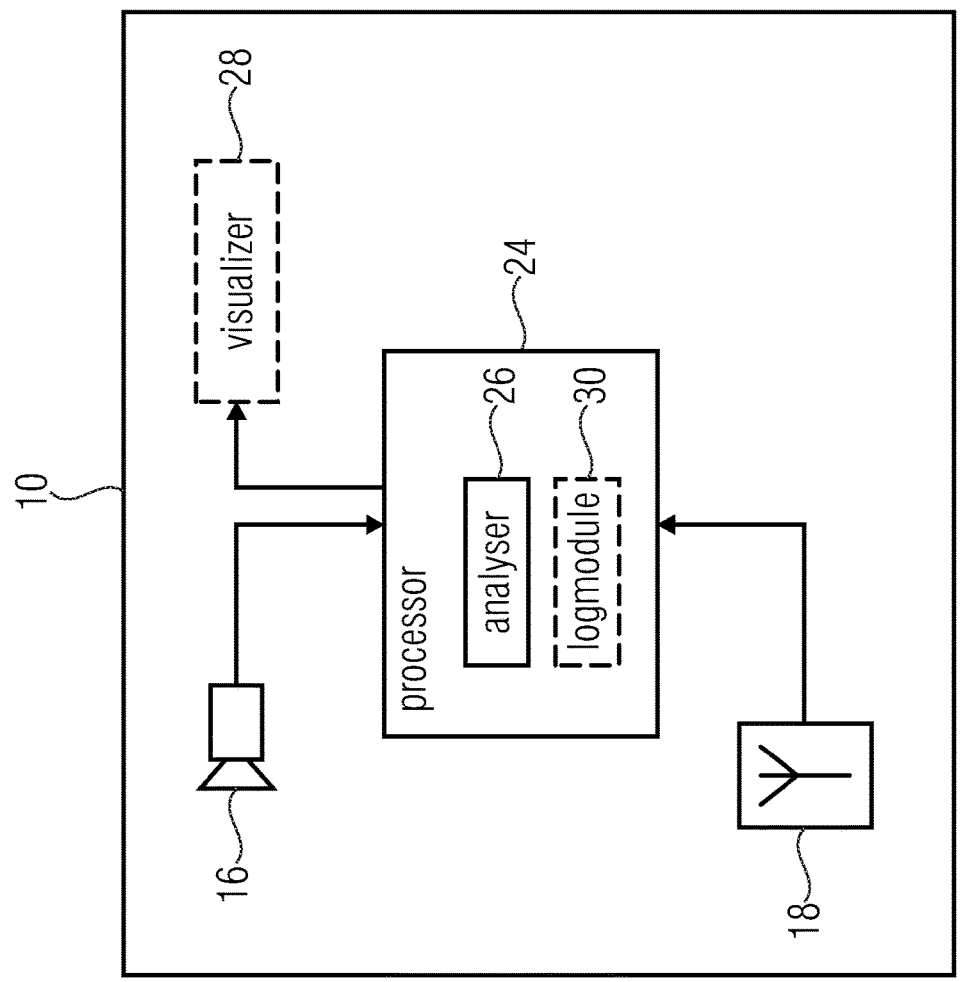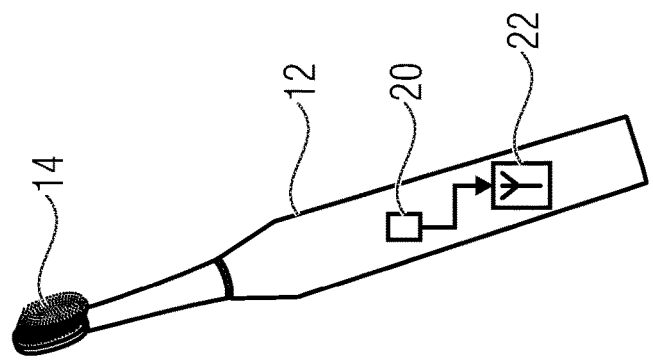
FIG 1

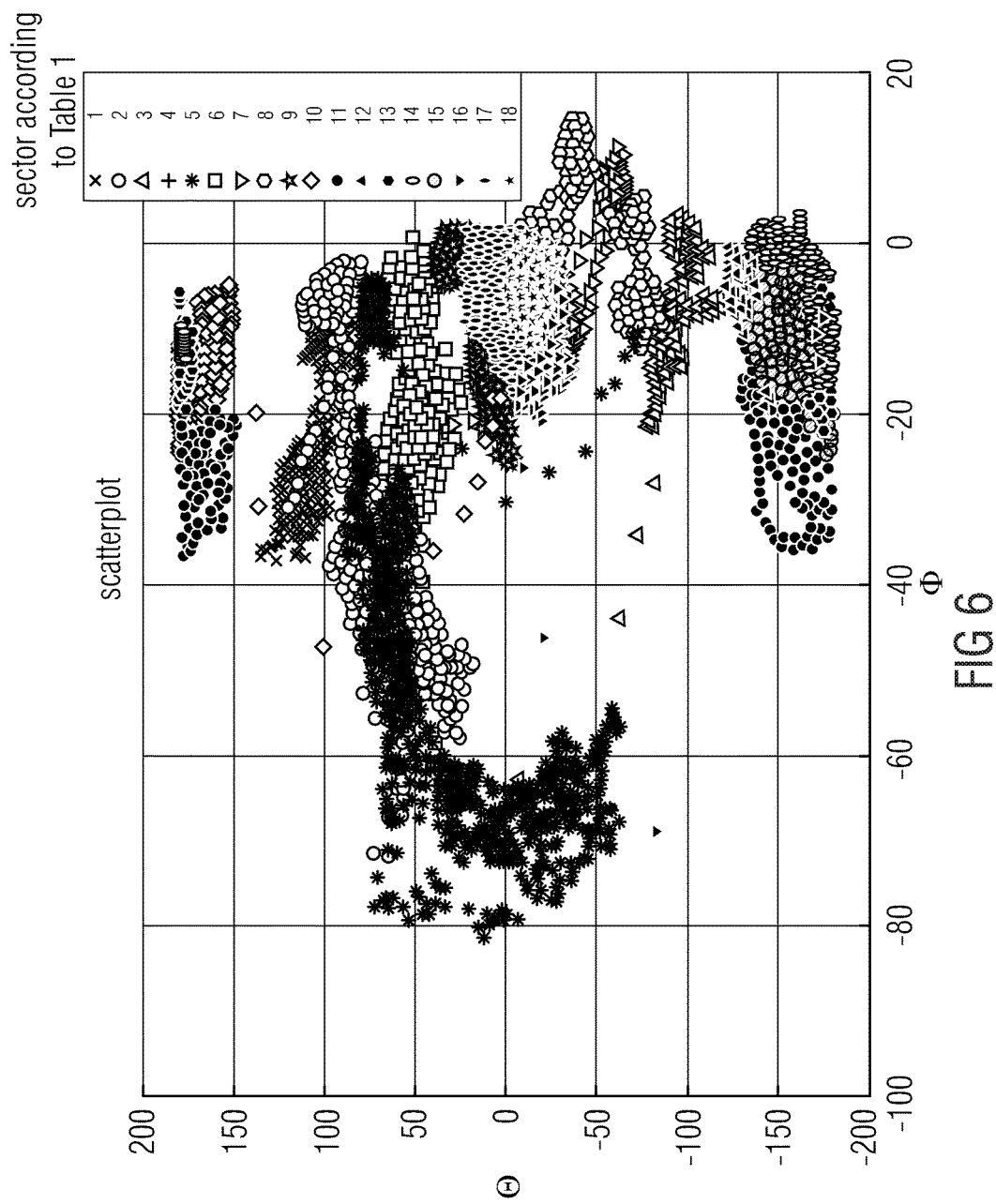

DETERMINATION OF A CURRENTLY TREATED BODY PORTION OF A USER

FIELD OF THE INVENTION

The present invention is concerned with a concept for determining a body portion of a user treated by the user using a personal hygienic device such as, for example, a toothbrush.

BACKGROUND OF THE INVENTION

It is known that, for various reasons, there is an increasing interest in the market of "smart devices", which assist the user in handling the respective device correctly. A "smart toothbrush", for example, could unburden parents from having to survey whether their children are brushing their teeth compliantly. For example, humans should brush their teeth regularly from a timing and frequency point of view and correctly in terms of the right brushing technique and coverage such as twice a day for 2 minutes with, at each time, covering all teeth and brushing the teeth evenly distributed across the 2 minutes.

Accordingly, there is a need for concepts allowing the provision of personal hygienic devices, such as toothbrushes, shavers or the like, with smart functions. However, in order to find enough acceptance in the market, the concept should allow for an easy and inexpensive implementation. Personal hygienic devices such as a toothbrush are occluded to a large extent when viewing the user during treatment using the respective personal hygienic devices what causes problems in video based tracking systems like in [13]. Moreover, location determination systems which may be built into personal hygienic device are either expensive or do not determine the location of the respective personal hygienic device sufficiently so as to determine the head portion of the user currently treated using the device.

Naturally, the needs and demands just-outlined also occur with respect to other personal hygiene devices that are used on other parts of the body—not only head or face.

Accordingly, there is a need for a concept for determining a body portion of a user treated by the user using a personal hygienic device, wherein the concept allows for an inexpensive implementation. The knowledge about the head portion treated by the user may, for example, allow for assisting the user in performing the treatment.

SUMMARY OF THE INVENTION

In accordance with one aspect there is provided an apparatus for determining a body portion of a user treated by the user using a personal hygienic device, comprising
 a camera configured to capture the user to obtain a pictorial representation of the user while treating the body portion using the personal hygienic device;
 an interface configured to receive sensor data from at least one inertial sensor residing in the personal hygienic device; and
 an analyzer configured to analyze the pictorial representation and the sensor data to determine the body portion.

In accordance with another aspect there is provided a system comprising an apparatus mentioned above and the personal hygienic device.

In accordance with another aspect there is provided a method for determining a body portion of a user treated by the user using a personal hygienic device, comprising
 capturing the user to obtain a pictorial representation of the user while treating the head portion using the personal hygienic device;
 receiving sensor data from at least one inertial sensor residing in the personal hygienic device; and
 analyzing the pictorial representation and the sensor data to determine the body portion.

In accordance with another aspect there is provided a computer program for performing, when running on a computer, the method mentioned above.

BRIEF DESCRIPTION OF THE DRAWINGS

Example implementations of the present application are the subject of the dependent claims. Moreover, example embodiments of the present application are described further below with respect to the figures, among which FIG. 1 shows an apparatus for determining a head portion of a user currently treated by the user using a hygienic device along with the hygienic device in accordance with an embodiment;

FIG. 6 shows a scatter plot example of estimated roll and pitch angles for the eighteen classes/sectors of Table 1 having been obtained using training data of three test persons during a training phase;

DETAILED DESCRIPTION OF THE INVENTION

Figure 2:
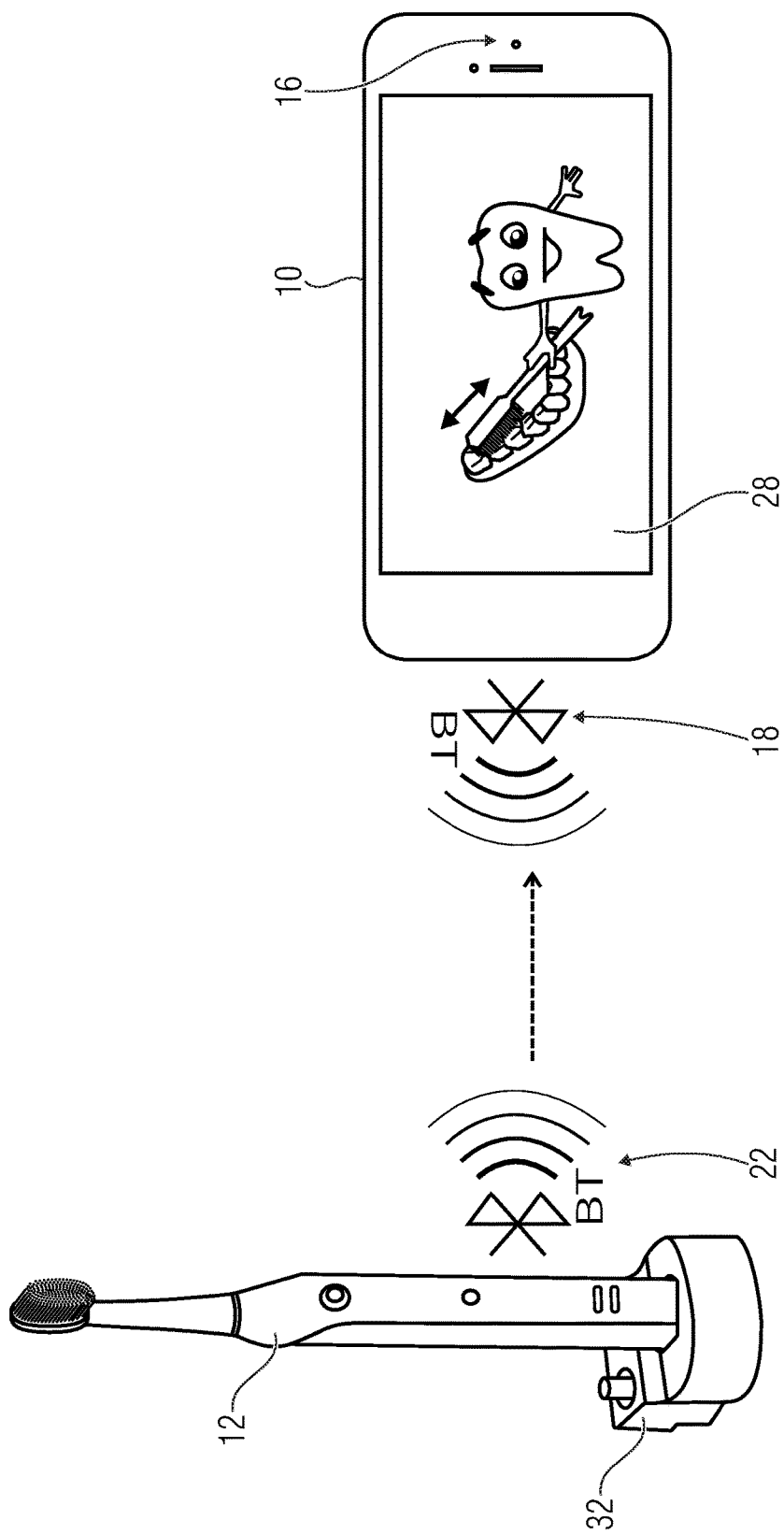
FIG. 2 shows a possible implementation for the hygienic device and apparatus of FIG. 1.

Embodiments of the present application described in the following exemplarily focus on determining the currently treated body portion of a user, currently treated by the user using a personal hygienic device, on or within the user's head (where within means within a cavity in the user's head, e.g. within the oral cavity). Accordingly, the embodiments are illustrated using examples like a toothbrush, shaver or the like as the personal hygienic device, but it should be clear that all these embodiments may be readily modified so as to operate in conjunction with other personal hygienic devices and, accordingly, other body portions currently treated. Merely representatively, the following description focuses on user's head related personal hygienic devices.

As described in the introductory portion, there is a need for a concept for determining a head portion (where "head portion" is used in the present description, it should be understood that this may generally be replaced by "body portion") of a user treated by the user using a personal hygienic device, wherein the concept allows for an inexpensive implementation. The knowledge about the head portion treated by the user may, for example, allow for assisting the user in performing the treatment. As illustrated using the subsequently explained embodiments, such a concept may be provided by, for example, exploiting that an increasing number of users already possess devices which, in turn, are provided with a camera and which allow for a supplementary addition of functions using this camera. Smartphones, for example, mostly comprise a camera and allow for a subsequent installation of further apps. Moreover, providing a device such as a personal hygienic device with an inertial sensor involves merely moderate costs as such inertial sensors are used in a widespread manner in a manifold of devices. Combining a pictorial representation of the user while treating his/her head portion using a personal hygienic device and acceleration measurement data as obtained from an inertial sensor residing in the personal hygienic device thus comes at low cost. However, the combination of the two sources for determining the user's head portion currently treated complement each other in that one source compensates weaknesses of the other source and vice versa. For example, owing to occlusions of the personal hygienic device in the camera's field of view, the camera might be an unreliable source for distinguishing situations at which the user treats predetermined different head portions. The acceleration measurement data, in turn, allows for a quite secure recognition of which of the situations currently applies. The same may be true the other way around: the acceleration measurement data may form an unreliable source for distinguishing certain head portions currently treated, the distinguishing of which, however, may be achieved more securely on the basis of the additionally provided pictorial representation of the user while treating the head portion using the personal hygienic device.

FIG. 1 shows an apparatus 10 for determining a head portion of a user treated by the user using a personal hygienic device, and FIG. 1 also shows the personal hygienic device 12. Apparatus 10 and personal hygienic device 12 form a system. In the example of FIG. 1, the personal hygienic device 12 is an electronic toothbrush, i.e., a toothbrush comprising an electronically swinging head of bristles 14, but as also stated further below, alternative embodiments of the present application may be readily derived on the basis of the description set out below by transferring the details thereof relating to a toothbrush as the personal hygienic device onto a combination of apparatus 10 with any other personal hygienic device, such as a toothbrush having no electronically derive bristle head or some other personal hygienic device for a treatment of a human head, such as a shaver, a face massage tool or any other facial hygienic device.

The apparatus of FIG. 1 comprises a camera 16 configured to capture a scene showing the user's face with the user currently treating a certain head portion using hygienic device 12. Camera 16 may be a still picture camera or a video camera. Accordingly, the pictorial representation showing the user while treating the head portion using hygienic device 12 may comprise one or more still pictures or a video composed of a sequence of frames/pictures.

Apparatus 10 further comprises an interface 18 configured to receive acceleration measurement data from an inertial sensor 20 residing, in turn, in hygienic device 12. Interface 18 may, as illustrated in FIG. 1, be configured to wirelessly receive the acceleration measurement data from inertial sensor 20. To this end, hygienic device 12 may be provided with a communication interface 22 inter-connected to the inertial sensor 20 so as to receive the acceleration measurement data from the inertial sensor 20 and operative to wirelessly send-out the acceleration measurement data to be received by interface 18 of apparatus 10. However, interface 18 may alternatively use a wired connection to receive the acceleration measurement data from the inertial sensor 20.

Further, apparatus 10 comprises a processor 24 coupled to camera 16 and (wireless) interface 18 and assuming the task of the analyzer 26, the functionality of which is described further below. In particular, the analyzer 26 analyzes the pictorial representation as obtained by camera 16 and the acceleration measurement data as received via interface 18 from inertial sensor 20 and determines, based on same, the head portion currently treated by the user using the personal hygienic device 12.

As described hereinafter with respect to a concrete example for a hardware implementation of the system and the apparatus shown in FIG. 1, apparatus 10 may for instance be implemented on a portable computer or portable communication device, such as a smartphone, which houses camera 16, interface 18 and processor 24. Processor 24 may for instance be a microprocessor with the analyzer 26 being implemented as an application or computer program which, when executed by processor 24, causes the processor 24 to perform the functionality of analyzer 26 as described in more detail below. Alternatively, some or all functionalities of analyzer 26 may be implemented externally, such as external to the portable computer or the portable communication device housing camera and interface. For example, such externally performed functionalities of analyzer 26 could be executed on a server configured to receive the pictorial representation and the acceleration measurement data via the internet or some other network. By way of outsourcing such functionalities to outside apparatus 10 may allow for considerably reducing the current consumption of apparatus 10 thereby allowing for battery savings.

For the sake of completeness, it is noted that FIG. 1 shows that the apparatus 10 may optionally comprise a visualizer 28 for visualizing the currently treated head portion to the user or for visualizing to the user an information indicating, for each candidate head portion of a set of candidate head portions, the temporal measure or a measure of remaining treatment demand for the respective candidate head portion determined based on the temporal measure. For instance, visualizer 28 may comprise a display or monitor. Additionally, processor 24 may optionally assume the task of a log module 30 for logging, for each of the just mentioned set of candidate head portions, the temporal measure of how long the respective candidate head portion has been determined to be the head portion by the analyzer 26, i.e. during what temporal duration.

Thus, the apparatus 10 of FIG. 1 is able to determine the head portion of a user currently treated by the user using hygienic device 12. In the case of hygienic device 12 being a toothbrush as depicted in FIG. 1 and as it is the exemplary case with the more detailed description of more specific embodiments outlined further below, the currently treated head portion is, for instance, a certain portion of the dentition of the user, such as, for instance the lower jaw left side portion of the user's dentition or the like. In the case of the hygienic device 12 being a shaver, the head portion currently treated, for instance, may be a certain portion of the beard portion of the user. In the case of the hygienic device 12 being, for instance, a facial massage device, the currently treated head portion is for instance any portion of the user's face.

As will be outlined in more detail below, the usage of camera 16 and inertial sensor 20 as a source for automatically determining the currently treated head portion leads to a mutual compensation of both sources weaknesses. For instance, the pictorial representation obtained using camera 16 allows analyzer 26 quite reliably to determine whether the currently treated head portion lies within the user's left hand side or right hand side, while the pictorial representation is an unreliable source for analyzer 26 to locate the currently treated portion in terms of its vertical position. To the contrary, the acceleration measurement data obtained by inertial sensor 20 might provide the analyzer 26 with the opportunity to reliably discriminate situations where the currently treated head portion differs in position along the vertical axis, while the acceleration measurement data may be an unreliable source for determining whether the currently treated head portion is on the left hand side or right hand side. Analyzer 26, by combining both information sources, i.e. pictorial representation and acceleration measurement data, is able to determine the currently treated head portion more reliably in terms of both left/right hand side discrimination and with respect to a discrimination of different positions along the vertical axis of the user.

According to the embodiments further outlined below, the analyzer 26 is configured to perform the determination of the currently treated portion by selecting the currently treated head portion out of a predetermined set of candidate head portions. In a manner outlined in more detail below, for instance, the analyzer 26 has to be "trained" to be able, when being fed using the pictorial representation stemming from camera 16 and the acceleration measurement data stemming from inertial sensor 20, to select the currently treated head portion out of a predetermined set of candidate head portions. The set of candidate head portions may coincide with the set of candidate head portions used for training. Alternatively, the set of candidate head portions out of which analyzer 26 selects the currently treated head portion may represent a coarser partitioning of an interesting portion of a human head. Details in this regard are described further below. For training analyzer 26, analyzer 26 may be implemented as a neural network or may have been trained using a statistical method. In any case, the predetermined set of candidate head portions represents a partitioning of an interesting portion of a human head, i.e. a partitioning which spatially subdivides an interesting portion of a human head into non-overlapping segments. For example, in the case of a toothbrush as hygienic device 12, the interesting portion of the human head partitioned into the set of candidate head portions out of which analyzer 26 selects a currently treated head portion might be the user's dentition. In case of the hygienic device 12 being a shaver, the predetermined set of candidate head portions may represent a partitioning of the user's beard area. In the case of the hygienic device being a facial massage device, the predetermined set of candidate head portions out of which analyzer 26 performs the selection represent a partitioning of the user's face.

As just mentioned, the effect of determining the currently treated head portion based on an analysis of both pictorial representation and acceleration measurement data is the mutual leveling of weaknesses in terms of spatial left/right discrimination and spatial discrimination along the vertical axis, respectively. Accordingly, the predetermined set of candidate head portions may for instance partition an interesting portion of a human head into four or more candidate head portions. That is, the set of candidate head portions out of which analyzer 26 performs the selection may comprise "at least" four candidate head portions, for example, namely: a first candidate head portion laying at the user's left hand side, a second candidate portion lying at the user's left hand side, but being displaced relative to the first candidate head portion along the user's vertical axis, a third candidate head portion lying at the user's right hand side, and a fourth candidate head portion lying at the user's right hand side, but being displaced relative to the third candidate portion along the user's vertical axis. For instance, in the case of the hygienic device 12 being a toothbrush, the first candidate head portion may be an upper jaw left side portion of the user's dentition, the second candidate portion may be a lower jaw left side portion of the user's dentition, the third candidate head portion may be an upper jaw right side portion of the user's dentition, and the fourth candidate head portion may be a lower jaw right side portion of the user's dentition. The set of candidate head portions out of which analyzer 26 performs the selection may additionally comprise a fifth candidate head portion, namely the front portion of the user's dentition, or a fifth and sixth candidate head portion, namely the upper jaw front portion and the lower jaw front portion of the user's dentition. In the case of hygienic device 12 being a shaver, for example, the first candidate head portion may be the user's left side cheek, the second candidate head portion may be the left side of the user's chin, the third candidate head portion may be the user's right side cheek and the fourth candidate head portion may be the right side of the user's chin. A fifth portion may then represent a frontal side of the user's chin. A sixth candidate head portion may represent the part between nose and mouth. In the case of the hygienic device 12 being a facial massage device, the set of candidate head portions, in addition to the portions mentioned with respect to the shaver as an example for the hygienic device 12, may comprise the forehead as a candidate head portion.

FIG. 2 shows a specific implementation example of the system and apparatus shown in and described with respect to FIG. 1. As already denoted above, the hygienic device is here assumed to be a toothbrush, but the description brought forward below may readily be modified so as to arrive at other implementations with a hygienic device 12 other than a toothbrush.

FIG. 2 shows hygienic device 12 as a battery driven toothbrush or power toothbrush, the toothbrush battery being rechargeable by placing the toothbrush 12 onto a socket 32. Apparatus 10 is embodied in FIG. 2 as a smartphone housing camera 16, the processor (not depicted in FIG. 2) and interface 18. Interface 18 receives the acceleration measurement data from the toothbrush counterpart interface 22. The smartphone additionally comprises a visualizer 28 in the form of a display.

The apparatus 10 is able to gain information about which sector of the mouth or dentition the user of toothbrush 12 and apparatus 10 is currently brushing and for how long. Additionally, the apparatus could accompany the information thus gained with information about the brushing pressure, gathered, for example, by way of an additional force sensor in the toothbrush 12 (not shown in FIG. 1 or 2). The toothbrush 12 as provided with an inertial sensor is not depicted in FIG. 2 and may be placed anywhere within or on the toothbrush's 12 housing. The inertial sensor may be comprised by an inertial measurement unit IMU. In other words, the inertial sensor may be embodied by an inertial measurement unit IMU which comprises acceleration sensors and/or angular rate sensors and, optionally, magnetic field sensors. As an explicit example, a 3-axis accelerometer may be used as sensor 20, optionally accompanied by one or more multi-axis gyroscopes and one or more magnetometers. As depicted in FIG. 2, a Bluetooth data connection may exemplarily be used to interconnect interfaces 22 and 18.

With respect to the acceleration measurement data, it is noted that the so-called sensor fusion, i.e. the way of bundling all of the sensor data of the acceleration sensors and/or angular rate sensors into a set of data relating to a predetermined non-toothbrush related coordinated system such as a system registered to the vertical axis, may be performed within the toothbrush 12 or within the analyzer, i.e. within the apparatus or smartphone 10, respectively. Moreover, the sensor fusion may also turn acceleration measurements into velocity or locational data by some kind of integration so that the term "acceleration measurement data" shall be understood as encompassing any data gained by or originating from acceleration measurement using inertial sensor 20. For example, a data preprocessing performed in the toothbrush may aim at reducing the amount of data to be transferred via the interface 22. Alternatively, the whole classification/position determination might be executed in the toothbrush.

The data, i.e. the pictorial representation and the acceleration measurement data, is collected in the analyzer 26 synchronous with camera 16 and inertial sensor 20. It may be that the data from the two different sources, namely camera 16 and sensor 20, arrives asynchronously at processor 24 or analyzer 26 and that the processor 24 or analyzer 26 assumes responsibility for correctly temporally registering, or synchronizing, the two corresponding pieces of information, i.e. video and sensor data so as to puzzled them together.

Figure 3:
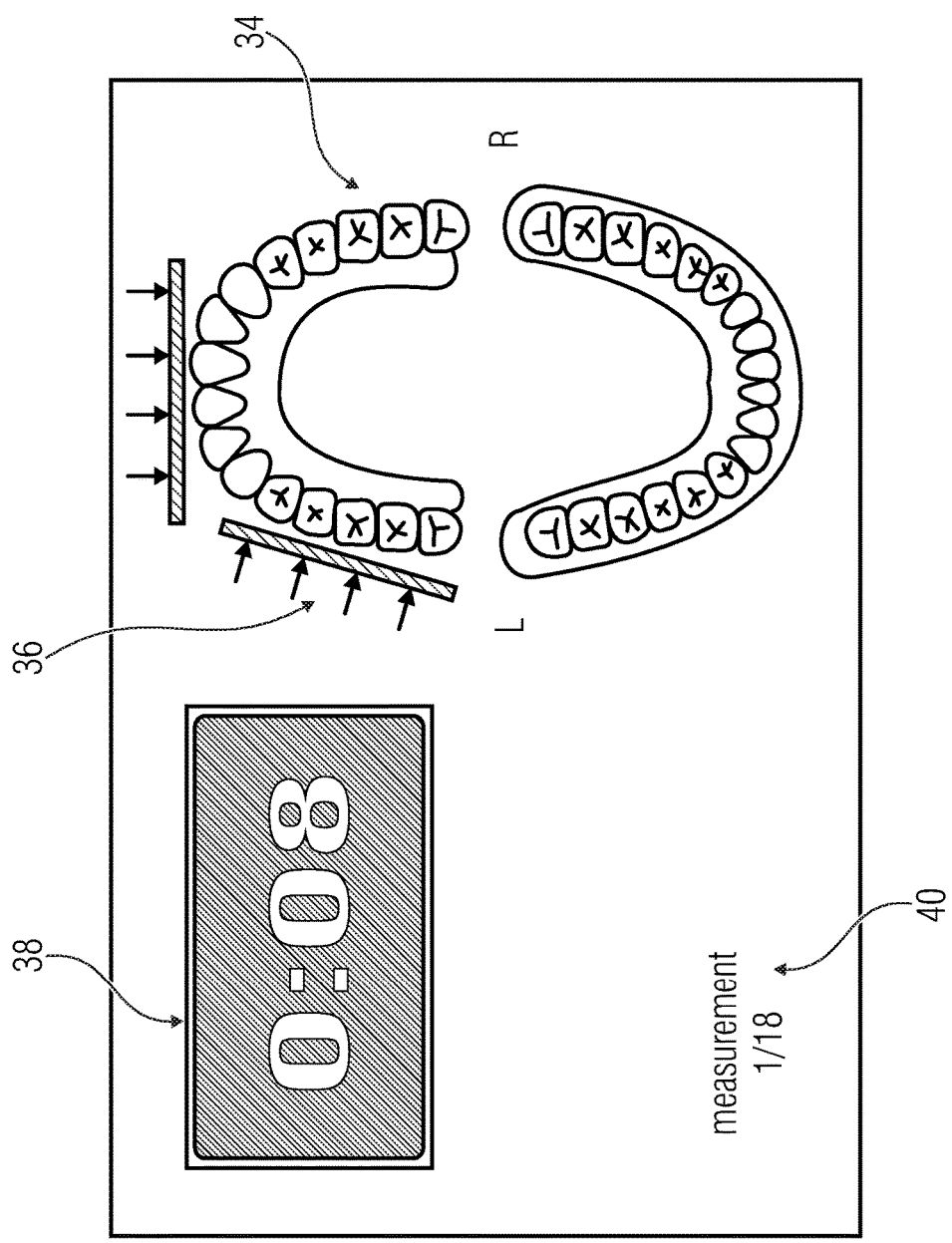
FIG. 3 shows a video snapshot of a video which could be used to instruct test persons for performing the data collection to train the analyzer in accordance with an embodiment.

Some data collection process may be used to train the analyzer 26. For example, in a process of data collection, a video may be shown to users, the video instructing the respective user to brush a specific brushing sector. The video may, for instance, show a screen such as the one visualized in FIG. 3. A dentition is depicted at 34 and some sort of highlighting 36 indicates to the test person which portion (section) of the dentition he/she shall treat, i.e. brush, using the toothbrush while collecting the data from camera 16 and inertial sensor 20. A remaining time duration during which the currently highlighted portion is to be brushed may be indicated at a section 38 of the video screen. At a portion 40, the video screen may indicate the number of discriminated candidate portions of the dentition to be sequentially brushed during the data collection process by the respective test person as well as the current candidate portion currently in line during the data collection process. In the case of FIG. 3, for example, the video currently shows that the first candidate portion of the test person's dentition is the outer side of the upper jaw left hand side of the dentition, this currently treated portion being the first portion of eighteen candidate portions with eight seconds remaining until the next candidate portion in line.

The collected data including the pictorial representation, namely the scene as captured by video 16 and the acceleration measurement data obtained by inertial sensor 20, is then used for training and testing the algorithms underlying analyzer 26, embodiments of which are described in more detail below. FIG. 3 illustrates that eighteen logical brushing sectors are used for training, for example.

The estimation/determination of the currently treated/brushed portion of a user may be, in a first stage, performed separately on the basis of the pictorial representation on the one hand and the acceleration measurement data on the other hand, and in a second stage both determinations are fused or combined in order to finally determine the currently treated/brushed portion more reliably. To this end, the eighteen brushing sectors of the training phase may, for instance, all be used internally for training the determination of the currently treated portion/sector of the dentition based on the inertial sensor, i.e. for training the sector for classification based on the inertial sensor.

The eighteen brushing sectors may, for instance, be defined as shown in Table 1.

TABLE 1 contains classes that represent a partitioning of a human dentition and, thus, represents an example for a set of classes of candidate head portions which could be used in the case of the personal hygienic device being a toothbrush.

| Nr. | Sector 1 | Sector 2 | Sector 3 |
| --- | --- | --- | --- |
| | Upper jaw outside | | |
| 1 | | | left side |
| 3 | | | right side |
| 2 | | | front |

TABLE 1-continued contains classes that represent a partitioning of a human dentition and, thus, represents an example for a set of classes of candidate head portions which could be used in the case of the personal hygienic device being a toothbrush.

| Nr. | Sector 1 | Sector 2 | Sector 3 |
|---|---|---|---|
| | chewing surface | | |
| 13 | | | left side |
| 15 | | | right side |
| 14 | | | front |
| | inside | | |
| 12 | | | left side |
| 10 | | | right side |
| 11 | | | front |
| | Lower jaw outside | | |
| 6 | | | left side |
| 4 | | | right side |
| 5 | | | front |
| | chewing surface | | |
| 18 | | | left side |
| 16 | | | right side |
| 17 | | | front |
| | inside | | |
| 7 | | | left side |
| 9 | | | right side |
| 8 | | | front |

According to Table 1, the eighteen brushing sectors are logically arranged along three dimensions, namely a dimension discriminating between upper and lower jaw, a dimension discriminating between the dentition's left and right hand sides and the frontal part, and a dimension discriminating between the internally facing side of the teeth, i.e. the side facing the tongue, the oppositely facing or outwardly facing side of the teeth and the chewing surface, respectively.

For instance, while the estimation of the currently treated portion on the basis of the acceleration measurement data is trained to discriminate all eighteen brushing sectors, the training may be related to a coarser partitioning of the dentition with respect to the estimation/determination of the currently brushed portion on the basis of the pictorial representation as obtained by the camera 16, such as a partitioning resulting from the eighteen sectors by pooling neighboring sectors of the eighteen sectors. Moreover, even the set of candidate sectors for which the visualization is performed later on with respect to the user, after having trained the analyzer 26, same may differ from the eighteen sectors. For instance, Table 2 illustrates a set of candidate sectors which might be used later on for visualization and the analyzer, respectively, which has been derived on the basis of the above-mentioned eighteen brushing sectors by reducing same to six classes. Beyond the five classes already mentioned above with respect to the dentition, a sixth class comprises "no brushing" is included.

TABLE 2 shows a table with an example for a reduced set of classes or candidate portions also relating to the case of the personal hygienic device being a toothbrush;

| Nr. of Class | Description |
|---|---|
| 1 | Upper jaw left side |
| 2 | Upper jaw right side |
| 3 | Lower jaw left side |
| 4 | Lower jaw right side |
| 5 | Front |
| 6 | No brushing |

Figure 4:
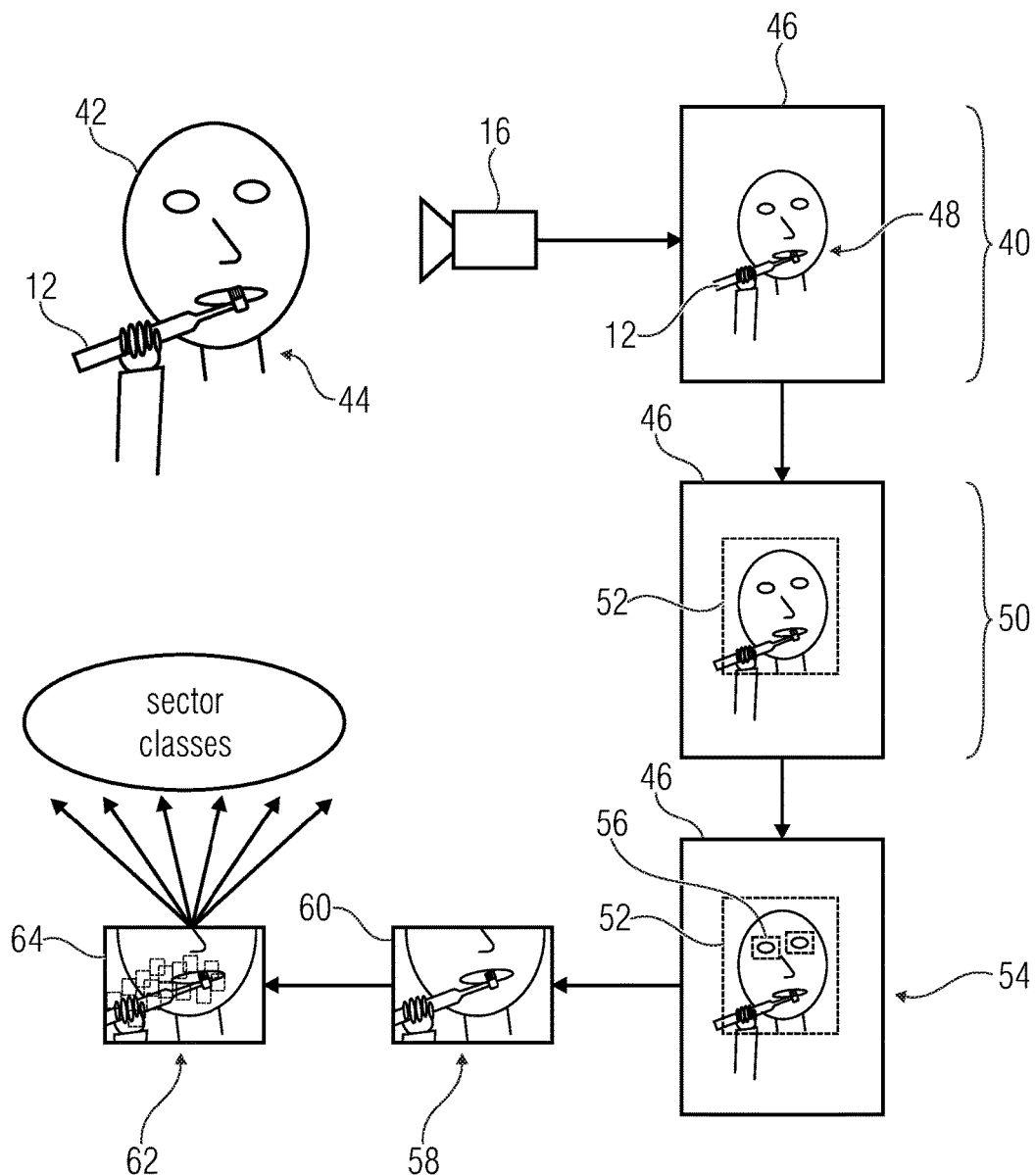
FIG. 4 shows a schematic diagram illustrating a sequence of steps performed by an analyzer so as to obtain a camera-based brushing sector classification in accordance with an embodiment.

With respect to FIG. 4, a mode of operation is described as to how the apparatus 10 of FIGS. 1 and 2 could operate in performing the brushing sector classification, preliminarily merely based on the camera.

At a first step of the overall brushing sector classification process, indicated at 40 in FIG. 4, the user 42 stays in front of the video capture device, namely camera 16, during brushing his/her teeth and is captured by the camera 16. That is, the scene 44 captured by camera 16 comprises the user 42 brushing the teeth using toothbrush 12. The pictorial representation thus obtained using camera 16 comprises one or more captured video pictures/frames. One captured video frame 46 is shown in FIG. 4. The picture 46 shows the user's 42 face holding the toothbrush 12 so that he latter extends into the mouth.

In particular, FIG. 4 concentrates on the camera-based brushing sector classification. Accordingly, the one or more video frames 46 are, in accordance with the embodiment of FIG. 4, passed to a face detection and tracking unit to subject same to a face detection and tracking process that locates the user's face 48 in the image or picture 46, this step being indicated at 50 in FIG. 4. After having determined a face region 52 within picture 46 in step 50, a facial feature localization unit of the analyzer 26 locates in a step 54 the eyes 56 within the face region 52. A face region normalization unit then, in a step 58, rotates and scales, i.e. warps, and cuts out a defined image region 60 out of picture 46, this region including and surrounding the mouth in the picture. The face region normalization may use the localized eye positions 56 in picture 46 as reference points. Finally, a brushing sector classification unit of analyzer 26 may extract in a step 62 features in the normalized image region 64, classify the image and provide a rating for each brushing sector that characterizes how likely it is that the user is currently brushing the associated sensor. FIG. 4, for instance, illustrates that the camera-based brushing sector classification may end-up into an estimation of the currently brushed portion which is selected out of six logical classes, namely the ones shown in Table 2.

In FIG. 4, steps 50, 54, 58 and 62 are performed by the analyzer 26. The individual steps described with respect to FIG. 4 are described in the following in more detail.

As already denoted above, the camera 16 can be any device that is capable of capturing a scene. It may, for instance, be a video camera that is capable of capturing an image sequence. The video camera may, for instance, be a mobile phone or a tablet, but also a camera connected to a computer. The video capture device 16 may be placed in front of the user for the sake of camera-based brushing sector classification such that the camera 16 captures the user while brushing their teeth. For example, the mobile phone shown in FIG. 2 could be placed in a mobile phone holder that is attached to the mirror in the bathroom. The video capture device could also be integrated in the mirror.

It could also be any other wearable device that has a camera, e.g. data glasses (e.g. Google Glass®) or smart watches. It captures the user and provides the image frames which are then subject to the face detection and tracking in step 50.

During the face detection and tracking in step 50, the image frames of the video capture device 16 are processed to locate the user's face in the image. The face detection can be implemented by using any of methods described in, for example, [3], [4] [5], [6], [9], [10]. The face detection provides the region 52 of the user's face 48 in the image 46 if the face 48 can be detected. If the image shows more than one face, the face detector can select the most prominent face in picture 46 by means of the face position or size in the image 46. For example, the biggest face in the image 46 could be selected as the user's face. The face detection could also select the face that is most similar to a user's face stored in a database. The face to be identified and tracked could be, for example, teached to analyzer 26 in a set up process. The face could also be characterized by gender, or age.

The face detection may also fail to detect the user's face in the picture 46. Reasons for failure can be, for example, bad illumination or occlusions of the face by the hand or toothbrush handle during brushing. When the face detection fails, the face can often still be tracked by face tracking. For example, the face can be tracked by finding the appearance of the face region 52 from the last frame within a neighborhood of the face location in the current frame as described in [8], for example. A face tracking can be implemented using any other method as well.

The face tracking can not only be used to increase robustness, but also to decrease the required processing power or energy consumption. This can be achieved by applying the face detection on occasional image frames and bridging the frames in between by applying to the latter face tracking. Reference is made to [11] to this end, for example. Face tracking is optional and can be omitted if the face detection, for example, already fulfills all of the requirements.

The facial feature localization in step 54 locates the eyes of the user in the image 46. It uses the face region 52 provided by the face detection and tracking process 50 and searches for the eyes only in the upper face region, i.e. the upper half of region 52. This reduces the search space and the required processing power and increases the robustness of the eye location. Facial feature localization may be implemented using any facial feature localization method and can in particular adopt the same algorithms that are used to detect the face region. Thereto, the algorithms can be trained to detect the left and right eye instead of the whole face region and can be applied only to a defined area relative to the detected upper face region. Any other method to locate facial features can also be used. For example, a method may be used that fits a 2D or 3D shape-model onto the image 46, i.e. parameters of the 2D or 3D shape model of a human face are adapted such that the image thereof, e.g. the projection, coincides with the actual image of the face in picture 46.

In contrast to the mouth region, it is unlikely that the upper face part is occluded by the user's hand during brushing the teeth. Therefore, it may support the described procedure to use facial features in the upper face region and not in the mouth region. Another implementation could not only locate the eye positions 56, but also other facial features, e.g. the eyebrows, the nose or the contour of the face.

The facial features often allow a more precise localization of the face than the face region provided by the face detection and tracking in step 50 and a better alignment for brushing sector classification. However, the facial feature localization may alternatively be omitted if the face detection in step 50 already fulfills the needs, for example.

The aim of the face region normalization 58 is to rotate, scale and cut-out a predefined region 60 around the mouth in picture 46. To this end, the facial features 56 as obtained by the facial feature extraction/localization process 54, may be used as reference points. In other words, the aim of the face region normalization 58 is to guarantee that the result thereof, i.e. the normalized image region 60, always shows the same part of the face and around the user's head that is relevant for classifying the brushing sector. It aims at removing at least some of the variances in the appearance of the user's face in the image that are caused by rotations of the head and movements of the user in front of the video capture device 16. Based on the reference points, the face region normalization involves transforming the image region 60 into the normalized image frame such that the facial features are mapped to the reference points that are predefined inside or outside the normalized image region. It can use only the eye locations 56 as reference points as well as any other combination of facial feature points to calculate the transform. Moreover, only the face region may be used for normalization if the facial feature localization is omitted.

The brushing sector classification 62 uses the normalized face region 60 which shows relevant parts of the user's face around the mouth and around the head and, while brushing, commonly also parts of the toothbrush and the user's hand. This is illustrated in FIG. 4. The appearance of the normalized face region 60 depends on the sector that is currently brushed, i.e. the currently treated portion of the user's head. For example, region 60 looks different whether the user is brushing the left or the right side of the dentition. The same holds for other sectors of the dentition. The brushing sector classification benefits from these differences in appearance to determine the sector that is currently being brushed. Features in the normalized image region 60 are extracted, classified and a rating is then provided for each candidate brushing sector of the set of candidate brushing sectors associated with the camera-based brushing sector classification. The rating characterizes how likely it is that the user is brushing the sector associated with the respective rating.

Any feature types can be extracted and used for classification: edges, brightness differences, census features or structure features or a combination thereof. Reference is made to [3], [4], [6], for example. The brushing sector classification implements one or more machine learning methods that learn how the normalized face region 60 typically looks for each sector of the teeth being brushed by evaluating the extracted features. Any machine learning method can be used to train the brushing sector classification, for example, boosting, support vector machines or neural-networks.

Typically, machine learning methods require annotated training data for learning: here, normalized face region samples with known or annotated brushing sectors may be used. The training samples can be generated by recording various users while brushing the teeth and extracting the normalized face regions. The brushing sectors shown in the training samples can be determined manually. The users can also be asked to brush the sectors of the teeth in a predefined order, as it was illustrated exemplarily with respect to FIG. 3, and length to enable automatic assignment of the brushing sectors to the training data.

The dentition can be split into two sectors discriminating, for example, merely between left and right or between top and bottom, or into three sectors discriminating, for example, merely between left, right and front, or into four sectors, namely the first four sectors of Table 2, or into five sectors, namely the first five sectors in Table 2, or into six sectors, namely the five top sectors of Table 2, however, dividing the fifth sector into the upper jaw and lower jaw front portion, respectively. Any other feasible number sectors may be used as well. Additionally, a separate class can be defined and trained, namely a class (none) that shows that the user is not brushing the teeth at all. Moreover, another classifier can be trained that is able to distinguish whether the user is brushing his teeth with the left hand or with the right hand.

As an output, the brushing sector classification unit can provide the sector that is currently brushed by the user. Moreover or alternatively, the camera-based brushing sector classification can provide a rating for each brushing sector that characterizes how likely it is that the user is currently brushing the associated sector.

In addition to the individual steps which could realize the camera-based brushing sector classification as just described with respect to FIG. 4, it may be supportive for the described procedure to estimate the head pose of the user in front of the camera 16. Several possibilities exist to estimate the pose.

In a 3D model fitting approach, a 3D face model is fitted to the 2D image 46 of the face. For example, parameters of a 3D model are adapted so that the projection thereof according to the optical projection parameters of camera 16 co-aligns with the appearance of the user's face in picture 46. For example, an algorithm as described in [1] may be used. Due to the high processing power requirements of such methods, it is often required to adopt less precise but faster algorithms.

A well-known method for 3D pose estimation from 2D images is POSIT. The POSIT algorithm is described in [2], for example. POSIT requires an approximate 3D model of the object, here the face, and the model's corresponding points in the 2D image to be known. POSIT requires at least 4 corresponding points to work. Due to the possible occlusion of the mouth during toothbrushing, the corners of the mouth cannot, or should not, be used as reliable feature points. In order to use the POSIT algorithm, suitable feature points may be found in the upper half of the face. There feature points may be determined during the facial feature localization 54.

Another possibility to perform post estimation is to determine the head pose by just considering the position and size of the detected eye regions 56. Having camera parameters and the average human eye distance, the translation in x, y, and z direction as well as the rotation around the y axis (bending the head to the side of the ear) can be calculated by standard mathematical operations, most importantly the intercept theorem. Determination of the rotation angle along the z axis (turning the head left or right) can use the relative detection size differences of the left and right eye to estimate the rotation angle. This is based on the fact, that eyes have different sizes in the image if the head is turned.

As described above, by face detection and tracking, the region of the user's face in the image frame 46 may be determined and used for the camera-based brushing sector classification. However, the position and size of the user's head in the image frame can also be used, for example, to check whether the user is positioned in the correct position in front of the video capture device 16. If necessary, the system can guide the user back into the right position of the image frame, e.g. into the center of the image or closer to the camera 16. In other words, the analyzer 26 may be configured to continuously survey a position of the user's face 48 in a field of view of camera 16 and to alarm the user in case of running the risk of leaving the field of view of camera 16 or a predetermined region of interest thereof, such as a certain region of the middle of the field of the view. For example, the alarm can start once the user comes close to the left, right, upper or lower border of the field of view of the camera 16. Additionally or alternatively, the alarm can start once the user is too close or too far from the camera. Additionally or alternatively, the region of the face 48 in the image 46 may also be used by the analyzer to check the illumination and to optimize the image quality. For example, the user could be asked to correct the lighting or the camera settings can be adapted according to the image properties within the face region. An implementation could adopt the method described in [7].

It is recalled that the camera-based brushing sector classification cannot only be applied to toothbrush devices. In fact, even the example of FIG. 4 could be adapted to other hygienic devices as well, such as classifying the position of a shaver in the face or the like.

After having described examples for performing the camera-based brushing sector classification, the following paragraphs deal with possibilities to perform the brushing sector classification on the basis of the inertial sensor.

In accordance with FIG. 5, main features for inertial sensor based brushing sector classification are the calculated roll and pitch angles. Roll and pitch are calculated based on acceleration measurements by inertial sensor 20 and using the direction of Earth's gravity vector as additional information.

Figure 5A:
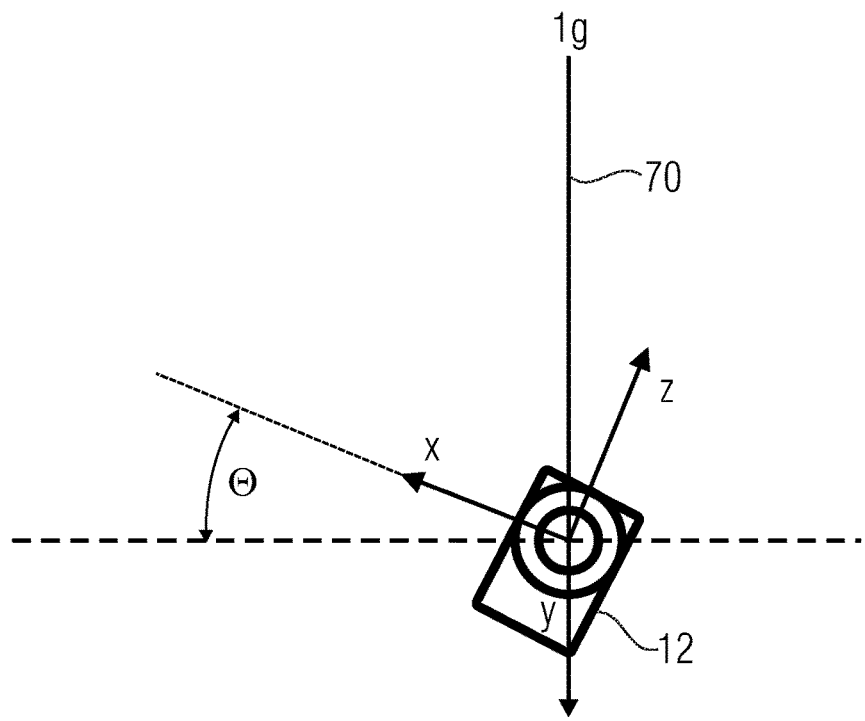
FIG. 5a shows a sectional view of a toothbrush perpendicular to a longitudinal axis of the toothbrush, registered so that the Earth's gravity vector runs vertically, so as to illustrate a roll angle.

As can be seen from FIG. 5*a*, the roll angle $\Theta$ may be defined as measuring a current tilt of the toothbrush 12 around its longitudinal axis with measuring, for example, the tilt using the vertical axis 70 as a reference. In FIG. 5*a* the vertical axis 70 is illustrated or denoted by an arrow denoted by "1g", this arrow symbolizing the Earth's gravity vector. For example, $\Theta=0$ may be defined as a situation where the bristles of the toothbrush face downwards, i.e. head into the direction of the Earth's gravity vector. In FIG. 5*a*, a toothbrush specific coordinate system is illustrated using a Cartesian coordinate system of axes x, y and z with axis y forming the longitudinal axis the toothbrush 12, the toothbrush's rotation around which is measured by $\Theta$ and axis z points into a direction opposite to the toothbrush bristles.

Figure 5B:
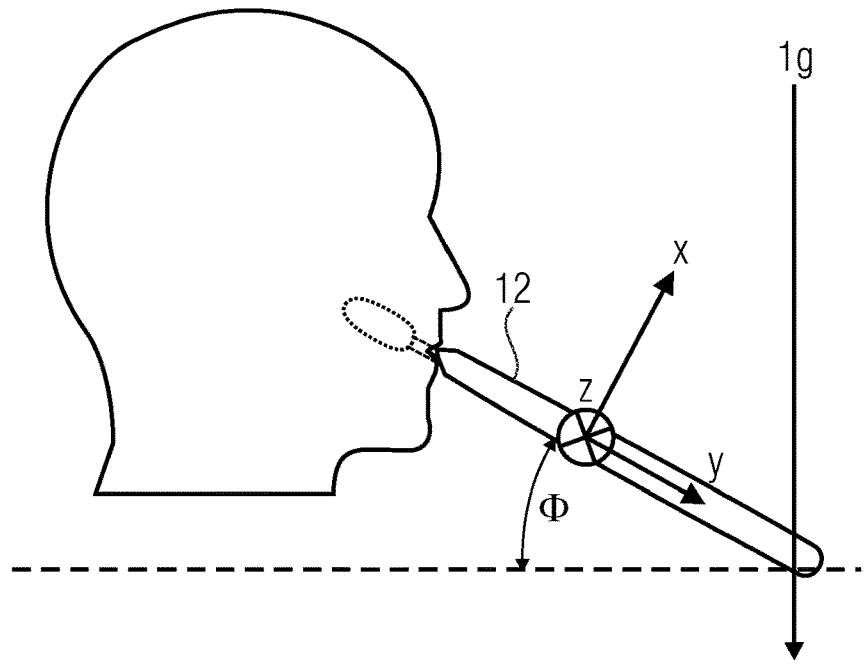
FIG. 5b shows a side view of user and toothbrush so as to illustrate the position of the pitch angle.

FIG. 5*b* uses the same nomenclature in order to illustrate how the pitch angle $\Phi$ could be defined. That is, coordinate system x, y and z is a local coordinate system of the toothbrush and vector "1g" corresponds to a vector pointing along the Earth's gravity. The horizontal plane, i.e. the plane normal to the Earth's gravity vector, i.e. a plane parallel to the horizon, is depicted as a dashed line in both FIGS. 5*a* and 5*b*. As can be seen from FIG. 5*b*, the pitch angle $\Phi$ measures the inclination of the toothbrush relative to the horizontal plane or, alternatively speaking, corresponds to $90°-\Phi$ angular deviation from the axis along which the Earth's gravity vector 1g points.

Figure 8:
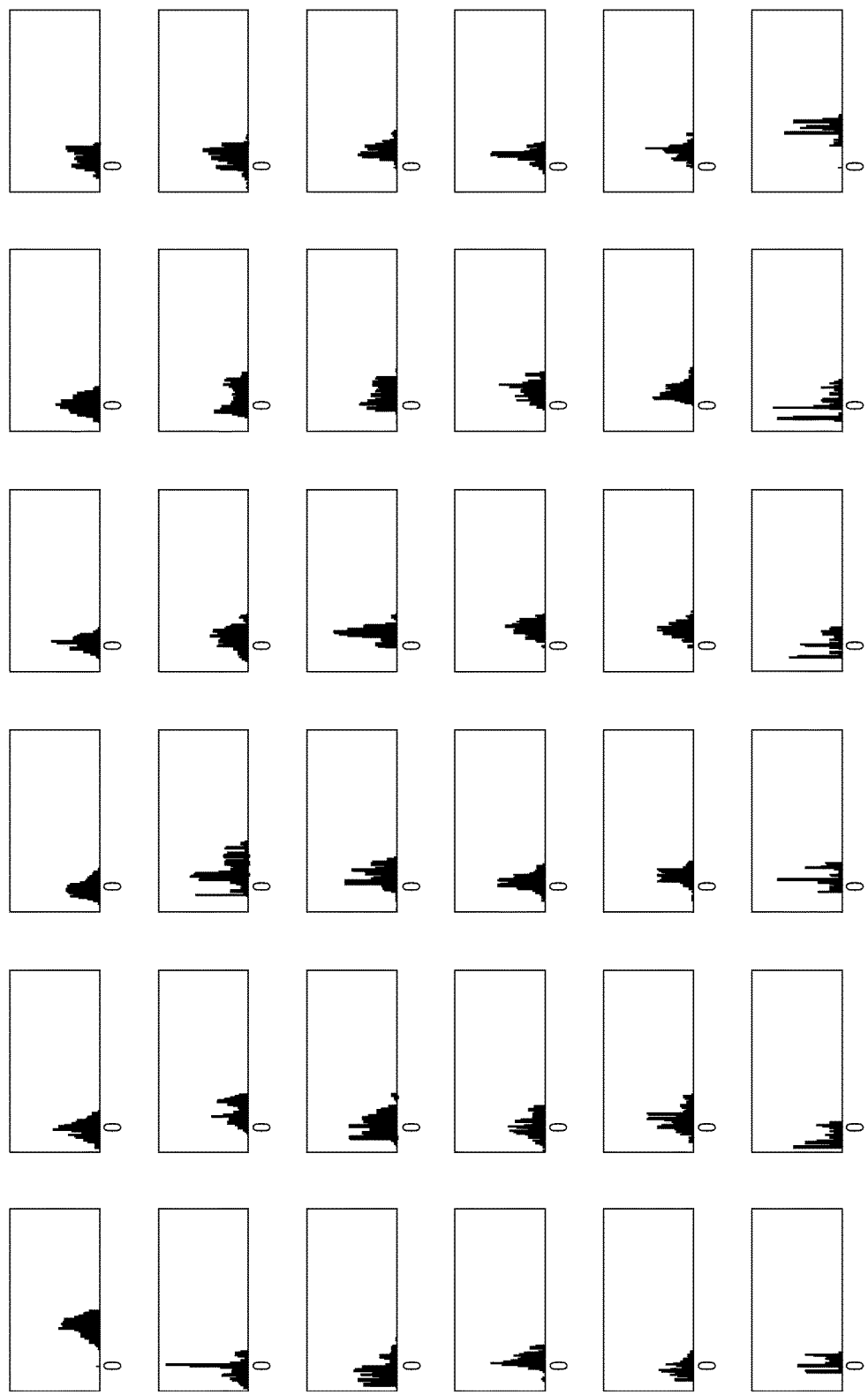
FIG. 8 shows probability distributions in the form of a confusion matrix: exemplary video output data for the 6 class model of Table 2 ended-up into these distributions, which have been divided into bins to prepare a calculation of probabilities of the camera-based classification result; the distributions of the diagonal represent the correct classification distributions; from top to bottom column, the distributions concern the actual brushing of class None, Left Top, Left Bottom, Right Top, Right Bottom, Front, and from left to right hand column, the distributions concern the scores for None, Left Top, Left Bottom, Right Top, Right Bottom, Front; each distribution plots 32 bins for the scores in arbitrary units along the horizontal axis and the associated number of times/tests for which at the respective actual brushing the respective brushing sector assumption, the respective score has been obtained, along the vertical axis in arbitrary units; the higher (positive) the score is, the more probable the score suggests that the currently brushed sector is the sector for which the respective score has been computed, i.e. to which the distribution (or column of distributions) belongs by which the respective score is comprised.

In a training phase mentioned above with respect to FIG. 3, labeled measurement data is, for example, collected in the defined eighteen brushing sectors. Using the training data, roll and pitch angles are calculated and the 18 class model is trained by mapping the data into the roll and pitch plane and derivation of characteristic values for the resulting distributions for each sector, e.g. mean and variance. An exemplary scatter plot is shown in FIG. 8. It is the result of mapping the data into the roll and pitch plane. In FIG. 6, the roll axis corresponds to the vertical axis, and the pitch axis corresponds to the horizontal axis. In addition to roll and pitch, other features could be used for sector classification based on acceleration measurement data, like mean values, variances, signal patterns, spectrum, etc. [13].

Thus, in accordance with an embodiment, the analyzer 26 performs an acceleration measurement data based brushing sector classification by calculating roll and pitch angles from the acceleration measurement data. Alternatively, the acceleration measurement data already represents roll and pitch angles. The roll and pitch angles are evaluated by analyzer 26 based on trained classifiers. For each candidate sector, a probability is calculated that this candidate sector is the current brushing sector. Alternatively, additional features of the acceleration measurement data, like mean values, variances, signal patterns, spectrum, etc. [13], may be used in addition to calculate a probability for each sector.

With respect to FIGS. 4 and 5a, b, camera-based and inertial sensor based brushing sector classifications have been described. The analyzer 26 may combine both classifications by way of a sensor fusion approach. The goal of applying sensor fusion is to compensate the weakness of one system with the strength of the other system. The sensor fusion process is exemplarily visualized in FIG. 7. The simplest way of sensor fusion applied by analyzer 26 may be to multiply the probabilities resulting for each brushing sector from the different classifications which are based on the different sensors, i.e. camera and inertial sensor, respectively.

Figure 7:
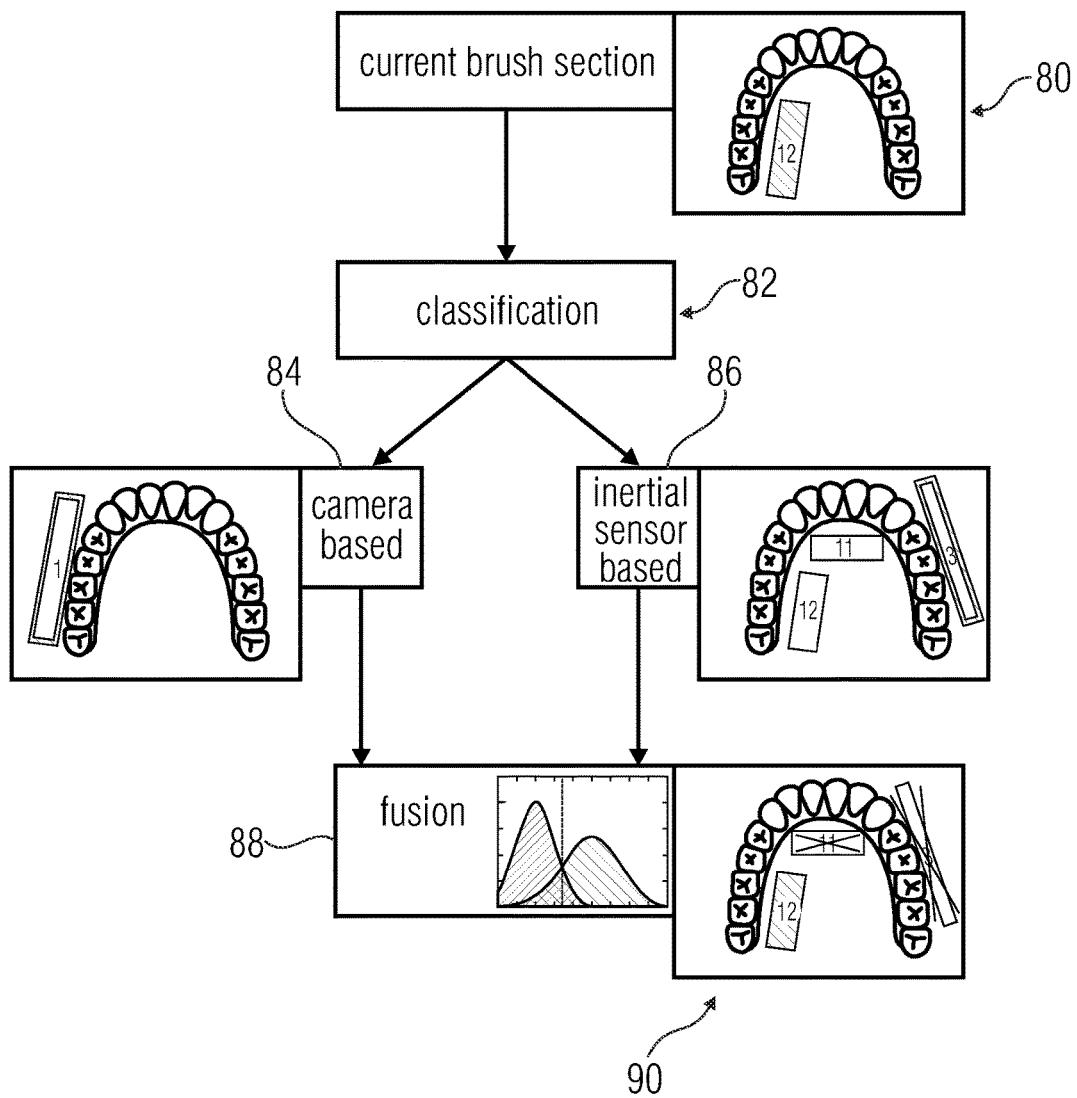
FIG. 7 shows schematically a possibility of separately performing camera-based and inertial sensor based determination of the currently treated portion and afterwards combining/fusing both determinations so as to end-up in a more reliable determination in which the weaknesses of the individual determinations are mutually compensated.

FIG. 7 illustrates at 80 that the currently brushed sector of the dentition is the sector with index 12 of the list of Table 1, i.e. the internal side of the left side of the upper jaw portion. As described above, the picture representation and the acceleration measurement data is received and recorded by analyzer 26. The classification is then performed separately at 8, thereby resulting in weight or probability values, namely one per candidate sector of the set of candidate sectors of the camera-based brushing sector classification, this set of probability values being indicated at 84 in FIG. 7, and a rate or probability value per candidate sector of a set of candidate sectors of the inertial sensor based brushing sector classification, with the latter set being indicated at 86 in FIG. 7. That is, the sector classifications are performed independently. FIG. 7 illustrates the case that the camera-based brushing sector classification determines a brushing on the left and that the inertial sensor based brushing sensor classification determines a brushing in sections 3, 11 or 12, applying the index nomenclature of Table 1. Beyond this, among the three sectors determined by inertial sensor based brushing sector classification, sector 3 is assigned the highest probability value. This is obviously not correct, as indicated at 80. However, by way of the sensor fusion 88, results 84 and the probabilities 86 are combined in such a manner that the final determination result or fused result is a correct classification of sector 12 as indicated at 90.

To enable sensor fusion of camera based brushing sector classification and inertial sensor brushing sensor classification, histograms for the calculated score value for a high amount of training data have been calculated. The resulting histograms are shown in FIG. 8 the sixth class model, i.e. the set of candidate portions available for the selection after fusion. Kernel density estimation has been performed based on the histograms to calculate conditional probability distributions for the confusion matrices presented in FIG. 8. Entries of the matrix can be read as follows: If the current brushing sector and the estimated class are the same then the corresponding distribution on the diagonal of the matrix is used. If the current brushing sector and the estimated class are different then the corresponding distribution does not lay on the diagonal. The first row in FIG. 8 shows the distributions for the current brushing sector "BrushNone", detected class (from left to right): "None", "LeftTop", "LeftBottom", "RightTop", "RightBottom" and "Front".

Figure 9:
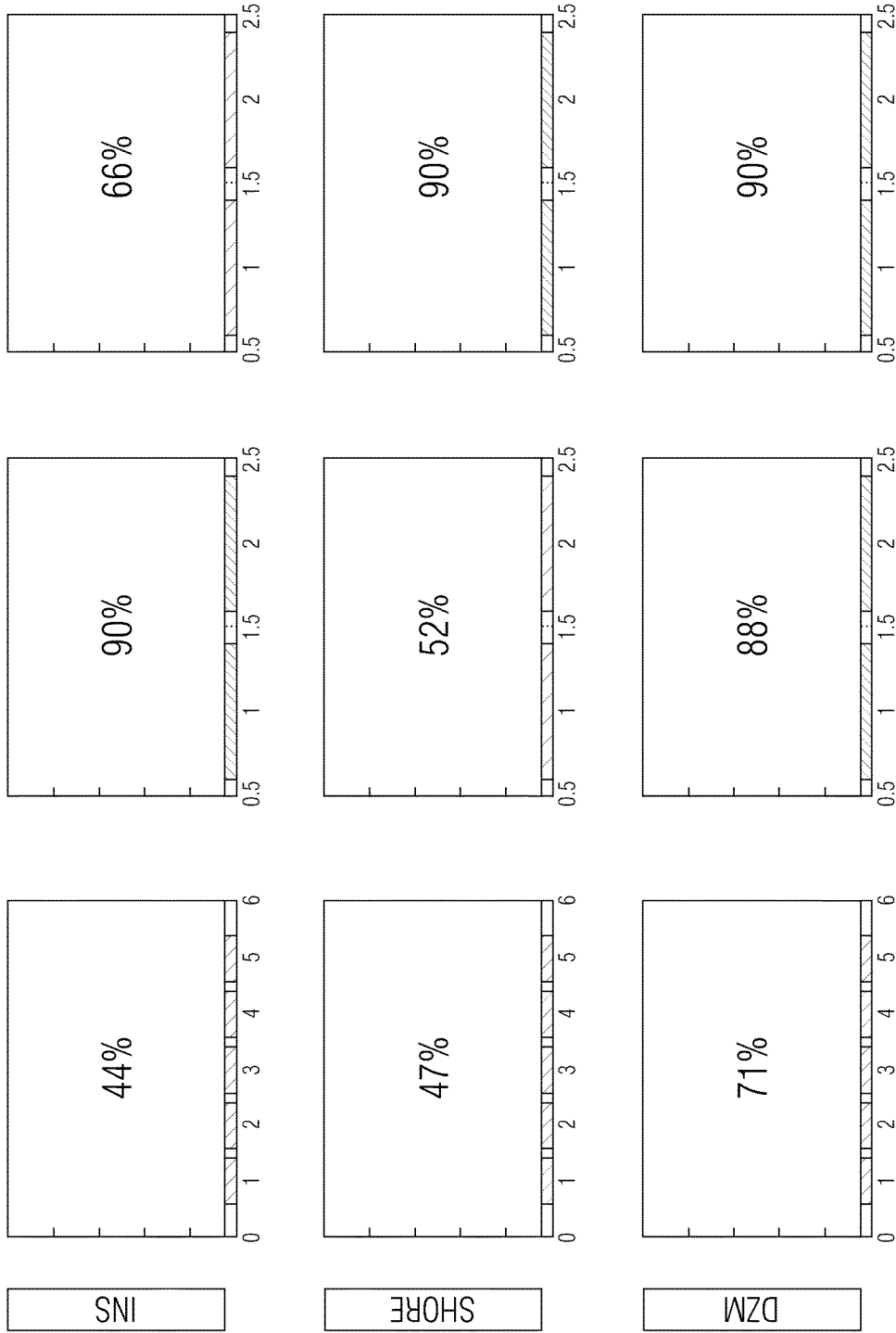
FIG. 9 shows a matrix of estimation results in terms of true rates for, from top to bottom, inertial sensors (INS), camera (SHORE) and sensor fusion (DZM; DZM=Dental zone monitoring) based classification using, from left to right, the 6 class model of Table 2 (1=up-left, 2=up-right, 3=low left, 4=low right, 5=front), upper and lower jaw classification (1 equals upper jaw; 2 equals lower jaw) or left and right side classification (1 equals left side; 2 equals right side)
Figure 10:
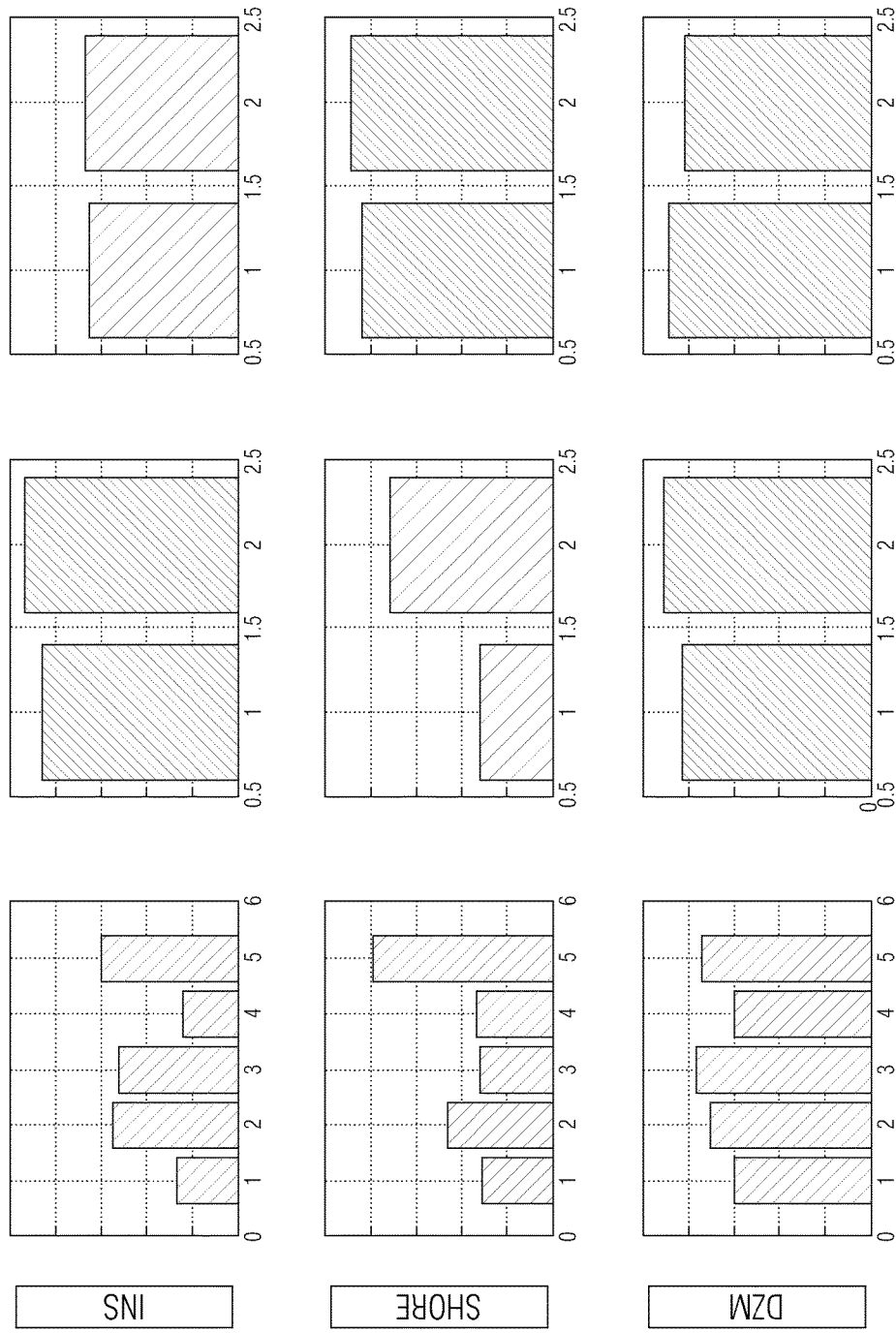
FIG. 10 shows a matrix of estimation results using data collected for inertial sensor (INS), camera (SHORE) and sensor fusion (DZM) in the matrix arrangement of FIG. 9 and using the models, with depicting in bar chart manner and using arbitrary units for the true rates/bar heights, the true rates for the individual classes.

The estimation results are presented in a matrix form as defined in FIG. 9. The true class rates for the classes up-left, up-right, low-left, low-right and front have been calculated. The separate classification rates of using inertial sensors (INS) and using the camera (SHORE) are presented together with the results of sensor fusion (DZM). For comparison and analysis, additionally the true classification rates for two simple models are presented: distinguishing upper and lower jaw or distinguishing left and right side. The overall classification rates of the models are displayed in the figure headings. In FIG. 10 for the SHORE 6 class model the overall estimation results are presented. Sensor fusion improves classification rates of the individual systems.

Figure 11:
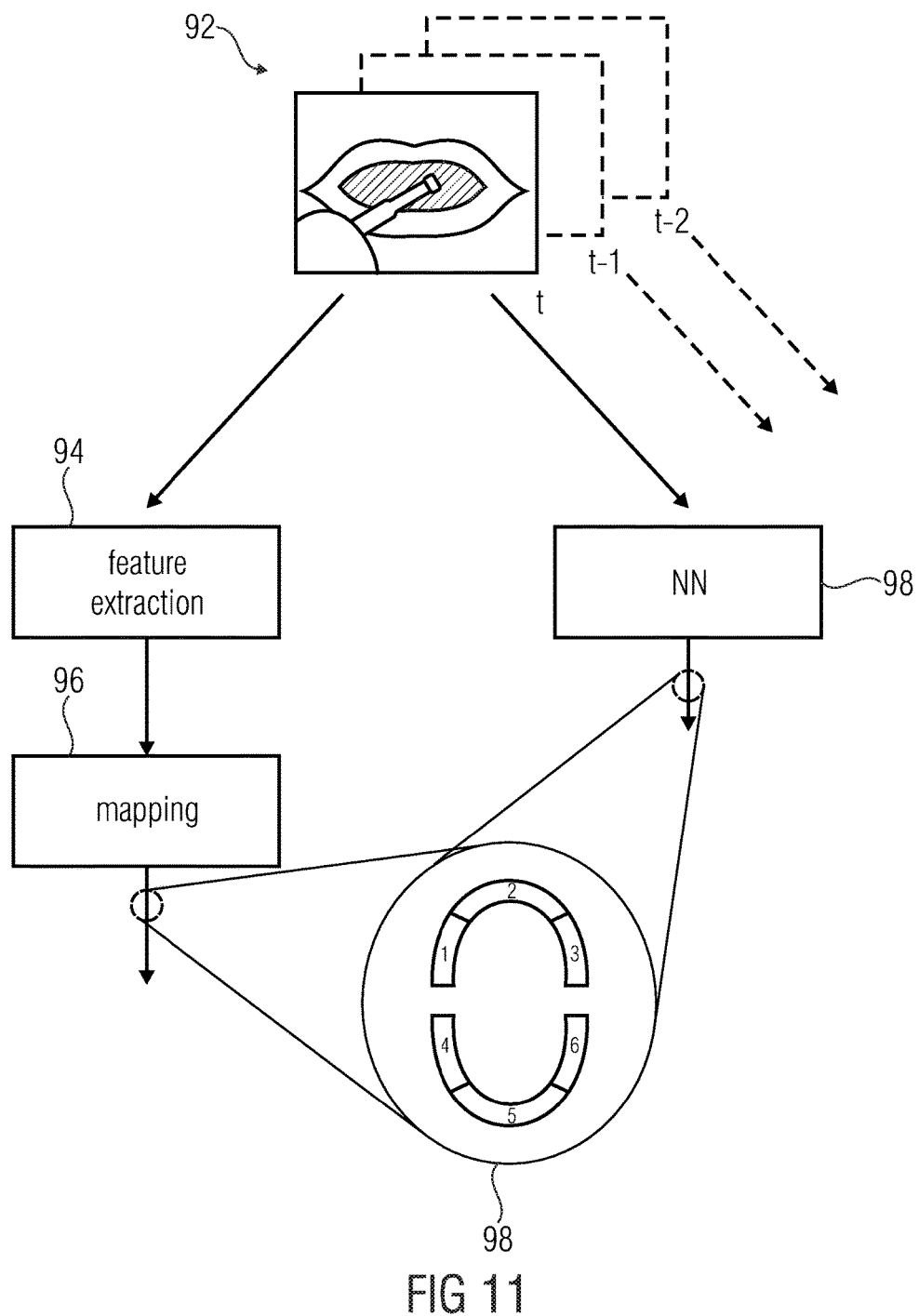
FIG. 11 shows a schematic diagram illustrating two alternatives for performing the camera-based evaluation analysis.

Thus, briefly summarizing and generalizing the above description, the following is noted. The analyzer 26 may be configured to subject the picture presentation stemming from the camera to a first evaluation analysis. This first evaluation analysis has been called camera based brushing sector classification or SHORE, but in the case of the hygienic device 12 not being a toothbrush, this nomenclature should obviously be adapted accordingly. The first evaluation analysis results in a first probability value for each candidate head portion of a first set of candidate head portions, each first probability value indicating how probable it is that the currently treated head portion is the respective candidate head portion of the first set to which the respective first probability value belongs. The first evaluation analysis is illustrated again with respect to FIG. 11. FIG. 11 shows at the top thereof the picture representation 92 comprising one or more pictures, each associated with a certain timestamp t. It should be mentioned that either each picture captured by camera could be made the subject to the first evaluation or merely a fraction thereof such as every second picture. The first evaluation analysis, i.e. the camera-based one, may treat each picture individually as described above and illustrated in FIG. 11 to result in one set of probability values. The update rate for the set of probability values would, thus, coincide with the rate of the pictures. According to an alternative approach, a sequence of pictures could be evaluated commonly to result in one set of probability values. The sequences thus subject to the first evaluation analysis could temporally overlap or not. The overlap could be such that two consecutively analyzed sequences are merely offset relative to each other by one picture so that the update rate for the set of probability values would, thus, coincide with the rate of the pictures. Alternatively, two consecutively analyzed sequences could be offset relative to each other so as to temporally abut each other without any overlap, so that the update rate for the set of probability values would, thus, correspond to the rate of the pictures divided by the number of pictures per sequence.

Two possibilities of realizing the first evaluation analysis are depicted in FIG. 11. The possibility illustrated at the left hand side corresponds to FIG. 4: each picture (alternatively each picture sequence) is subject to a feature extraction 94 followed by a mapping 96 of the resulting features onto the aforementioned probability values, namely one probability value per candidate sector of the set 98 of candidate sectors of the camera-based evaluation analysis. The feature extraction 94 includes, for example, folding the picture with certain feature templates to obtain a feature map from the respective picture. This feature map may be mapped by mapping 96 onto the probability values. The mapping 96 may be done by a neural network or by some other means, such as by determining the distance of the feature map according to some distance measure from representative feature maps, each being representative of a certain candidate sector offset 98. Alternatively, the respective picture (or the sequence of pictures) currently analyzed may be subject to the neural network directly, the neural network 98 yielding a score/probability value per candidate sector of set 98 directly.

FIG. 11 already illustrates that both alternatives for realizing the camera-based evaluation analysis, i.e. feature extraction followed by mapping or feeding a neural network directly, may start with a locating and extracting of the mouth region. For example, in the manner outlined above with respect to FIG. 4, namely using steps 50, 54 and 58, the mouth region may be located in, and extracted from, a picture of the pictorial representation 92, the mouth region including and surrounding the user's mouth. The mouth region may then be warped depending on a position of the user's face in the picture to correspond to a predetermined position of the user's face in the field of view of the camera. The determination of the currently treated head portion of the user on the basis of the warped mouth region may then be performed either using an alternative involving steps 94 and 96 or using the neural network 98.

Figure 12:
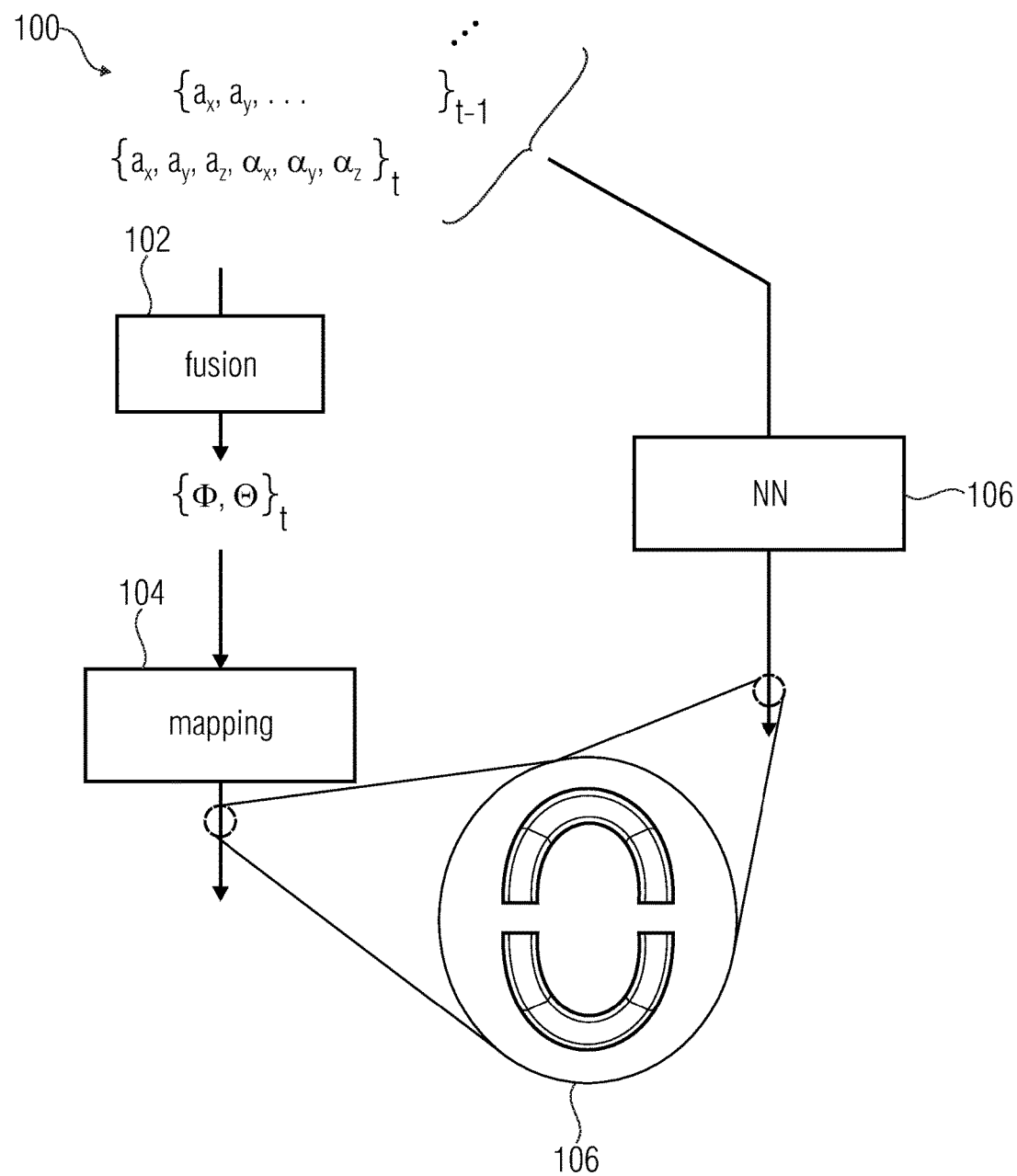
FIG. 12 shows two alternatives for performing the inertial sensor based evaluation analysis.

The description brought forward above revealed that the analyzer 26 may be configured to, separately from applying the first evaluation analysis of FIG. 11 onto the picture representation obtained by the camera 16, subject the acceleration measurement data of the inertial sensor 20 to a second evaluation analysis. FIG. 12 again illustrates the evaluation analysis operating on the acceleration measurement data. The acceleration measurement data as depicted in FIG. 12 at 100 may, for instance, represent a sequence of sets of linear and, optionally, rotational acceleration parameters measuring the acceleration of the hygienic device 12 along/around hygienic device specific local axes x, y and z. The sampling rate, for instance, may be equal to or differ from the picture rate of the pictorial representation 92. By sensor fusion 102 the analyzer 26 may turn the acceleration values into a representation comprising roll $\Theta$ and pitch $\Phi$ relating to a global or not-hygienic-device-specific coordinate system. A sequence of values for roll $\Theta$ and pitch $\Phi$ at a certain sampling rate may thus result. The fusion 102 may time-align or at least temporally associate the pictures of the pictorial representation 92 and the pairs of pitch and roll, respectively, so that each picture and an associated portion of the roll/pitch information forms a data item per time stamp.

A mapping 104 may then map the roll/pitch data, i.e. the data obtained by acceleration measurement, onto a probability value for each candidate portion of the set 106 of candidate portions used for the inertial sensor based evaluation analysis. The inertial sensor based evaluation analysis has been denoted above as inertial sensor based brushing sector classification or INS.

It should be noted that the mapping 104 may not be applied onto a single pair of roll and pitch sample values with then being repeated for each subsequent roll/pitch sample pair describing a respective instantaneous position of the toothbrush. In this case, namely, for each set 98 of probability values as obtained by the first evaluation analysis a set 106 of probability values would be determined by the second evaluation analysis solely determined by one instantaneous sample of roll and pitch at a time instant near or at the time stamp of the picture or picture sequence for which set 98 has been determined. Alternatively, the mapping 104 may be performed for each temporal sequence of roll/pitch values. The sequences are temporally determined by way of synchronization with the pictures of the pictorial representation, for example, i.e. so that they each temporal overlap with the time stamp of a respective picture or picture sequence for which the first evaluation analysis is performed.

Importantly, the instantaneous samples or the sequences of roll/pitch values, i.e. the temporal intervals of roll/pitch, in units of which the mapping 104 may be performed, are temporally placed irrespective, i.e. independent from, a content of the pictorial representation, e.g. irrespective of whether the user has just started brushing the teeth or not. Moreover, consecutive mappings 104 applied onto consecutive roll/pitch samples or temporal intervals are performed mutually independent as there is no need to locally "track" a path along which the toothbrush is moved in the mouth. Rather, each instantaneous roll/pitch sample is mapped onto probability value set 106 individually or each temporal sequence of roll/pitch values is mapped 104 onto the probability values for set 106 by recognizing certain characteristic patterns associated with the sections of set 106, independent from any other sequence of roll/pitch values.

The mapping 104 may use a neural network or some other statistical method, such as a clustering technique or the like, i.e. may be performed like mapping 96.

Similar to the description with respect to FIG. 11, alternatively the acceleration measurement data 100 may be subject to a neural network 106 directly, i.e. without any fusion 102.

As illustrated in FIGS. 11 and 12, the sets of candidate portions 98 and 106 for the camera-based and inertial sensor-based evaluation analysis may be different from each other. That is, they may represent different partitioning of a same interesting portion of the user's head, i.e. here exemplarily the dentition. However, alternatively, the sets are the same. By multiplying or otherwise suitably combining probability values relating to co-located candidate portions of the final set of candidate portions from which the currently treated head portion may finally be selected by the analyzer 26, analyzer 26 may fuse/combine the results of both evaluation analysis, thereby achieving the above outlined effect of mutually compensate weaknesses in the individual sources for determining the currently treated head portion.

Thus, by performing first and second evaluation analysis of FIGS. 11 and 12 as well as the data fusion/combination for each time-aligned data item, i.e. picture and associated roll/pitch pair or sequence of roll/pitch pairs, the analyzer 26 continuously updates the determination of the currently treated head portion so that the logging module 30 may log, for each candidate head portion of the final set of candidate head portions, i.e. the set relevant after data fusion, a temporal measure of how long the respective candidate head portion has been determined to be the currently treated head portion. Moreover, the visualizer may update the visualization of the currently treated head portion accordingly and/or the visualization of the candidate head portions which need more treatment or for updating the visualization of how long the respective candidate head portion has been treated already.

It should be noted that the analyzer 26, such as the analyzer's neural network, if any, may be taught in the field. That is, the analyzer 26 could be taught locally on the consumer's device to optimize the recognition of his individual face. This could, for example, improve the robustness of the face tracking and the position determination. In a setup process, the user could by led through a similar teaching process as the one by which the system was originally trained in the labs before shipment. The user would execute the learning cycle at home in his/her environment. The system learns characteristics of the user's face, his/her bathroom, his/her toothbrush and even his/her individual brushing style. The analyzer could then be modified locally or on a server. The modification could be done merely for the user alone or some ar all of the learning data could be used to improve the overall database. The overall database could be located on a server from which every analyzer 26 being used by users load the latest analyzer's software from.

Thus, the above description revealed that video/camera output score values can be processed to calculate probability distributions for the defined classes in a confusion matrix and that these distributions may be used for sensor fusion. Training data may be used to train the camera and acceleration sensor based classification. The classification results are obtained using the inertial sensor and the camera and are subject to sensor fusion. The above outlined embodiments do not need any additional starting position for the toothbrush. That is, the user is not urged to start brushing at a defined tooth, nor is the input of any initial information needed for the automatic determination of the currently treated portion. The brushing sector classification described above is, as far as the inertial sensor based side is concerned, applicable any time and does not need to track the position of the hygienic device continuously like in the case inertial navigation. No integration boundaries are necessary. Instead, using sector classification it is possible to calculate the likelihood for each sector using snapshot data of inertial and video data by evaluating the current measurements with the trained classifiers.

Further, no restrictions are made for toothbrushing. The user can brush his/her teeth as preferred and as accustomed to. The same applies in the case of any other hygienic device. This is achieved by the possible snapshot classification.

Further, using just inertial data collected with a sensor in hygienic device, already a brief classification of the currently treated portion can be calculated with the inertial sensor classification. This classification can then be improved by sensor fusion with the camera based classification. In the same manner, a brief classification is possible using only the camera-based classification, and improving this classification using the inertial sensor classification, in turn.

It should be noted that the inclusion of further sensors, such as magnetic field sensors (compasses) and angular rate sensors may improve the above mentioned embodiments. Estimation of the orientation (angles) of the power toothbrush can then be improved and further features like the compass azimuth angle can be added to be used for the classification in the same way as done using the acceleration data. Using additional angular rates an attitude filter, such as based on a Kalman filter, can be used to estimate the three-dimensional attitude of the hygienic device regarding the Earth's inertial coordinate system.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a digital storage medium, for example a floppy disk, a DVD, a Blu-Ray, a CD, a ROM, a PROM, a RAM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine readable carrier.

Other embodiments comprise the computer program for performing one of the methods described herein, stored on a machine readable carrier.

In other words, an embodiment of the inventive method is, therefore, a non-transitory computer readable medium for performing, when running on a computer, one of the methods described herein.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitionary.

A further embodiment of the inventive method is, therefore, a data stream or a sequence of signals representing the computer program for performing one of the methods described herein. The data stream or the sequence of signals may for example be configured to be transferred via a data communication connection, for example via the Internet.

A further embodiment comprises a processing means, for example a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods may be performed by any hardware apparatus.

The apparatus described herein may be implemented using a hardware apparatus, or using a computer, or using a combination of a hardware apparatus and a computer.

The methods described herein may be performed using a hardware apparatus, or using a computer, or using a combination of a hardware apparatus and a computer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

The above described embodiments are merely illustrative for the principles of the present invention. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCES

[1] J. Saragih, S. Lucey and J. Cohn, "Deformable Model Fitting by Regularized Landmark Mean-Shifts", International Journal of Computer Vision (IJCV), 2010.

[2] DeMenthon, D. & Davis, L. Sandini, G. (Ed.)"Model-based object pose in 25 lines of code," Computer Vision ECCV'92, Springer Berlin Heidelberg, 1992, pp. 335-343

[3] Christian Kueblbeck and Andreas Ernst: "Face detection and tracking in video sequences using the modified census transformation", Journal on Image and Vision Computing, vol. 24, issue 6, pp. 564-572, 2006, ISSN 0262-8856

[4] Christian Kueblbeck and Andreas Ernst: "Fast face detection and species classification of African great apes", AVSS 2011, IEEE 8th International Conference on Advanced Video and Signal-based Surveillance, Klagenfurt, 2011.

[5] U.S. Pat. No. 6,519,579; Reliable identification with preselection and rejection class, P. Plankensteiner and U. Dieckmann

[6] U.S. Pat. No. 8,320,682 B2; Evaluation of edge direction information, Bernhard Froeba and Christian Kueblbeck.

[7] EP1593001 B1; Adjustment of an image recorder with dynamic measuring fields, Christian Kueblbeck and Bernhard Froeba.

[8] EP2406697 A1; Verfahren und System zum Erkennen eines Objektes, und Verfahren und System zum Erzeugen einer Markierung in einer Bildschirmdarstellung mittels eines berührungslos Gestik-gesteuerten Bildschirmzeigers, Thomas Wittenberg and Christian MÜNZENMAYER and Christian KÜBLBECK and Andreas Ernst.

[9] DE102009048117 A1; Verfahren und Vorrichtung zum Erkennen einer Fehldetektion eines Objekts in einem Bild, Andreas Ernst and Christian KUBLBECK and Tobias Ruf.

[10] DE102009048118 A1; Verfahren und Vorrichtung zum Verwalten von Objektansichtsdaten in einer Objektdatenbank, Andreas Ernst and Christian KUBLBECK and Tobias Ruf.

[11] EP13178529.7; patent pending Jun. 30, 2013, apparatus and method for resource-adaptive object detection and tracking, Anton Papst and Andreas Ernst and Tobias Ruf and Jens Garbas.

[12] Bocksch, Marcus; Seitz, Jochen; Jahn, Jasper: Pedestrian Activity Classification to Improve Human Tracking and Localization. In: Proceedings of the 4th International Conference on Indoor Positioning and Indoor Navigation (IPIN), Montbeliard, France, 2013, S. 667-671

[13] U.S. Pat. No. 8,744,192 B2

What is claimed is:

1. An apparatus for determining a body portion of a user treated by the user using a personal hygienic device, the apparatus comprising:
    a camera configured to capture the user to obtain a pictorial representation of the user while treating the body portion using the personal hygienic device;
    an interface configured to receive sensor data from at least one inertial sensor residing in the personal hygienic device; and
    an analyzer configured to analyze the pictorial representation using a machine-learning method based on normalized face region samples with known or annotated sectors and to combine resulting pictorial data with the sensor data to determine the body portion.

2. The apparatus in accordance with claim 1, wherein the analyzer is configured to perform the determination by selecting the body portion out of a predetermined set of candidate body portions.

3. The apparatus in accordance with claim 2, wherein the set of candidate body portions at least comprises:
    a first candidate head portion lying at the user's left hand side;
    a second candidate head portion lying at the user's left hand side, but being displaced relative to the first candidate head portion along the user's vertical axis;
    a third candidate head portion lying at the user's right hand side;
    a fourth candidate head portion lying at the user's right hand side, but being displaced relative to the third candidate head portion along the user's vertical axis.

4. The apparatus in accordance with claim 2, wherein the personal hygienic device is a toothbrush and the set of candidate body portions at least comprises
    an upper jaw left side portion of the user's dentition,
    a lower jaw left side portion of the user's dentition,
    an upper jaw right side portion of the user's dentition, and
    a lower jaw right side portion of the user's dentition.

5. The apparatus in accordance with claim 1, wherein the pictorial representation comprises one or more pictures, and the analyzer is configured to associate a time-aligned portion of the sensor data to each of the one or more pictures to obtain a time-aligned mixed pictorial/acceleration data and determine the body portion based on the time-aligned mixed pictorial/acceleration data.

6. The apparatus in accordance with claim 1, wherein the analyzer is configured to
   subject the pictorial representation to a first evaluation analysis to obtain a first probability value for each of a first set of candidate body portions indicating how probable the body portion is the respective candidate body portion of the first set of candidate body portions,
   subject the sensor data to a second evaluation analysis to obtain a second probability value for each candidate body portion of a second set of candidate body portions indicating how probable the body portion is the respective candidate body portion of the second set of candidate body portions, and
   select the body portion out of a third set of candidate body portions on the basis of the first probability values and the second probability values,
   wherein the first, second and third sets of candidate body portions represent an identical partitioning or a different partitioning of a portion of a human head.

7. The apparatus in accordance with claim 1, wherein the body portion is a head portion and the analyzer is configured to
   locate from a picture of the pictorial representation, and extract from the picture, a mouth region, the mouth region including and surrounding the user's mouth, and warp the mouth region depending on a position of a face of the user in the picture so as to correspond to a predetermined position of the user's face, and
   determine the body portion on the basis of the warped mouth region.

8. The apparatus in accordance with claim 1, wherein the analyzer is configured to calculate a roll and pitch of the personal hygienic device on the basis of the sensor data, and determine the body portion on the basis of the roll and pitch.

9. The apparatus in accordance with claim 1, wherein the pictorial representation comprises a sequence of pictures each associated with a predetermined time stamp and the analyzer is configured to associate a time-aligned portion of the sensor data to each of the sequence of pictures to obtain a sequence of time aligned mixed-pictorial/acceleration data items having a time aligned mixed-pictorial/acceleration data item per time stamp and update a determination of the body portion for each time aligned mixed-pictorial/acceleration data item.

10. The apparatus in accordance with claim 1, wherein the analyzer is configured to continuously survey a position of the user in a field of view of the camera and to alarm the user in case of running the risk of leaving the field of view of the camera or a predetermined region of interest thereof.

11. The apparatus in accordance with claim 1, further comprising a visualizer configured to visualize to the user the body portion currently treated.

12. The apparatus in accordance with claim 1, further comprising
   a log module configured to log, for each candidate body portion of a set of candidate body portions, a temporal measure of how long the respective candidate body portion has been determined to be the body portion by the analyzer, and
   a visualizer configured to visualize, for each candidate body portion, the temporal measure or a measure of remaining treatment demand for the respective candidate body portion determined based on the temporal measure, to the user.

13. A system comprising an apparatus according to claim 1 and the personal hygienic device according to claim 1.

14. A method for determining a body portion of a user treated by the user using a personal hygienic device, comprising:
   capturing the user to obtain a pictorial representation of the user while treating the body portion using the personal hygienic device;
   receiving sensor data from at least one inertial sensor residing in the personal hygienic device; and
   analyzing the pictorial representation using a machine-learning method based on normalized face region samples with known or annotated sectors and to combine resulting pictorial data with the sensor data to determine the body portion.

15. A non-transitory computer readable medium for performing, when running on a computer, the method of claim 14.

* * * * *